United States Patent
Varga

(10) Patent No.: US 10,821,009 B2
(45) Date of Patent: Nov. 3, 2020

(54) VASCULAR MEDICAL DEVICE, SYSTEM AND METHOD

(71) Applicant: Swiss Capital—Engineering AG, Zürich (CH)

(72) Inventor: Michael Szente Varga, Zumikon (CH)

(73) Assignee: Swiss Capital—Engineering AG, Zürich (CH)

( * ) Notice: Subject to any disclaimer, the term of this patent is extended or adjusted under 35 U.S.C. 154(b) by 0 days.

(21) Appl. No.: 15/166,141

(22) Filed: May 26, 2016

(65) Prior Publication Data

US 2017/0340461 A1 Nov. 30, 2017

(51) Int. Cl.

| | |
|---|---|
| *A61F 2/852* | (2013.01) |
| *A61F 2/856* | (2013.01) |
| *A61F 2/07* | (2013.01) |
| *A61F 2/954* | (2013.01) |
| *A61F 2/82* | (2013.01) |
| *A61F 2/06* | (2013.01) |
| *A61F 2/89* | (2013.01) |

(52) U.S. Cl.
CPC ............... *A61F 2/852* (2013.01); *A61F 2/07* (2013.01); *A61F 2/856* (2013.01); *A61F 2/954* (2013.01); *A61F 2/89* (2013.01); *A61F 2002/061* (2013.01); *A61F 2002/072* (2013.01); *A61F 2002/826* (2013.01); *A61F 2210/0076* (2013.01)

(58) Field of Classification Search
CPC .......... A61F 2/852; A61F 2/844; A61F 2/856; A61F 2/95; A61F 2/954; A61F 2002/828; A61F 2002/826; A61F 2002/065
See application file for complete search history.

(56) References Cited

U.S. PATENT DOCUMENTS

| | | | | |
|---|---|---|---|---|
| 5,824,040 | A * | 10/1998 | Cox .................... | A61F 2/07 623/1.35 |
| 2002/0019659 | A1* | 2/2002 | Goicoechea .......... | A61F 2/07 623/1.11 |
| 2006/0155358 | A1* | 7/2006 | LaDuca ................ | A61F 2/856 623/1.11 |
| 2008/0097578 | A1* | 4/2008 | Erickson .............. | A61F 2/07 623/1.16 |

(Continued)

FOREIGN PATENT DOCUMENTS

| | | |
|---|---|---|
| EP | 2815722 A1 | 12/2014 |
| WO | WO2004/019823 A1 | 3/2004 |
| WO | WO2010/111666 A1 | 9/2010 |

OTHER PUBLICATIONS

WIPO, European International Search Authority, International Search Report and Written Opinion dated Jul. 13, 2017 in International Patent Application No. PCT/EP2017/062809, 13 pages.

(Continued)

*Primary Examiner* — Tan-Uyen T Ho
*Assistant Examiner* — Chima A Igboko
(74) *Attorney, Agent, or Firm* — Inskeep IP Group, Inc.

(57) ABSTRACT

The present application discloses a covered stent and a method for navigating the covered stent to a branch vessel, the covered stent comprising a main body and at least one lateral side branch connected to the main body, wherein the lateral side branch is flexible and expandable. A system of covered stents and a method for interconnecting the covered stents is also disclosed.

22 Claims, 12 Drawing Sheets

(56) References Cited

U.S. PATENT DOCUMENTS

2010/0268327 A1* 10/2010 Bruszewski .............. A61F 2/07
623/1.18

OTHER PUBLICATIONS

European Patent Office, Extended European Search Report dated Sep. 12, 2016 in European Patent Application No. 16171467, 6 pages.

* cited by examiner

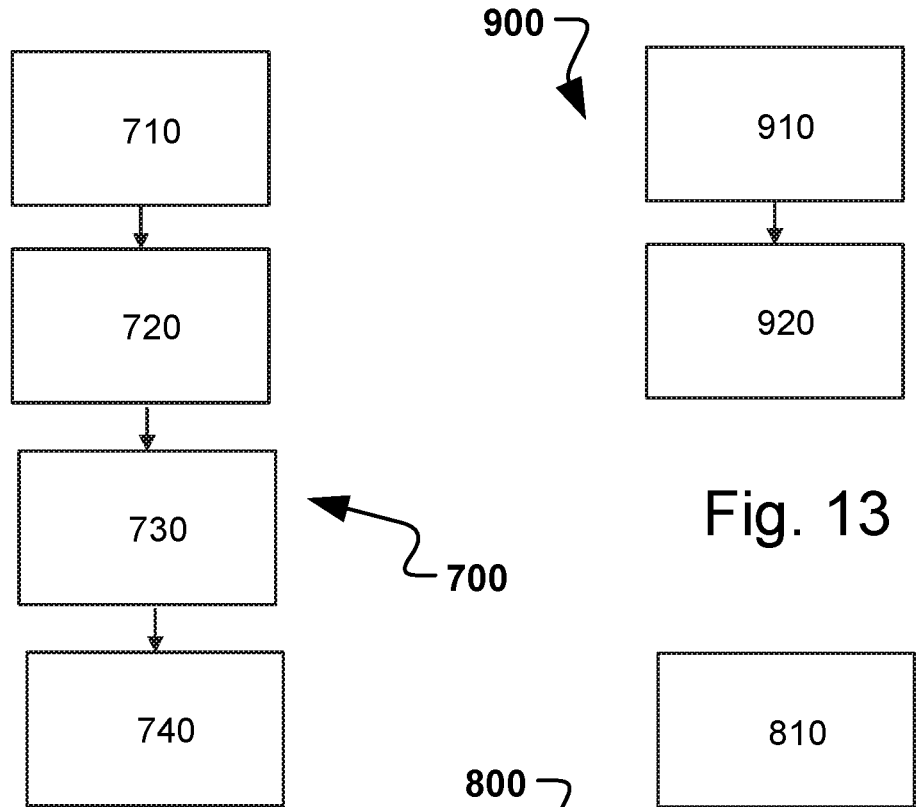
Fig. 12A
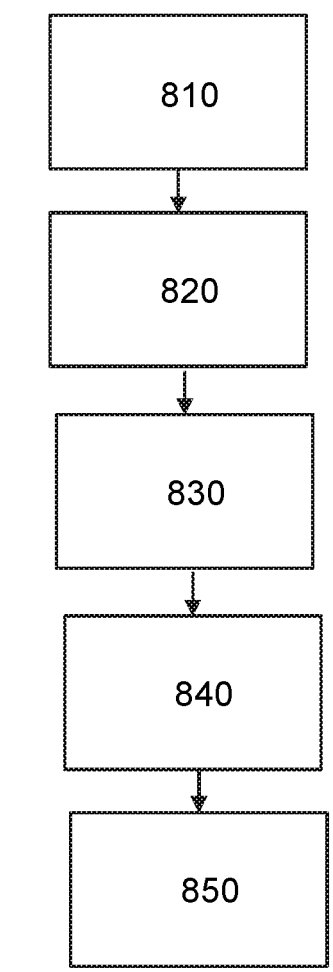
Fig. 13
Fig. 12B

VASCULAR MEDICAL DEVICE, SYSTEM AND METHOD

BACKGROUND OF THE INVENTION

Field of the Invention

This disclosure pertains in general to the field of medical devices. More particularly the disclosure relates to a vascular medical device being a covered stent, stent graft or endoprosthesis for liquid communication with one or more side branch vessel(s), and a system of such devices, as e.g. multiple covered stents for assembly with each other, and for deployment at a target site in a patient. Also, medical procedures for deploying such devices and systems are disclosed. The target site in a patient includes for instance at least a portion of an aorta of a patient. More particularly, treatment of at least a portion of an aorta of a patient by implantation of such a device or system in a medical procedure is disclosed. The medical procedure is preferably minimally invasive.

Description of the Prior Art

It is known to use modular covered stents or stent grafts for treatment or repair of vascular disease, such as e.g. an aneurysm. WO 2005/027784 discloses a system of modular covered stents for implantation in a diseased vessel, where the covered stents have apertures along the midsection of the covered stent. The apertures are used for aligning with branch vessels of a main vessel so that further stents can be connected at an aperture from a main vessel stent. The apertures need to be precisely aligned with the ostia of the side vessels. From the main vessel stent, a further stent graft protrudes then from each aperture into the branch vessel.

An undesired issue with such known devices is that it is difficult for the operator to correctly implant a covered stent in a main vessel aligned with branch vessels. Apertures or branches from the main vessel covered stent have to be correctly positioned in the main vessel in relation to the position of the branch vessels. The branch vessel is to be in liquid communication with the main vessel, i.e. through branch vessel covered stents or portion of a larger stent graft unit with arms to the branch vessels. The main vessel covered stent is expanded and thus implanted in the main vessel.

Once expanded and deployed, the main vessel covered stent cannot be re-positioned. Misaligned apertures or branch covered stents misaligned with branch vessels may for instance cause kinking of the branch vessel covered stent. This kinking may cause undesired reduced blood flow to the branch vessel. It may also deteriorate durability and length of life of the covered stent when implanted, caused by pulsatile flow. It may also lead to leakage, or loosening of a side branch covered stent unit from a main vessel modular covered stent.

Moreover, there is a certain risk of damaging the vessel when the operator is trying to find branch vessels using modular covered stents and there is a certain misalignment. Prior art modular covered stents with apertures pose a further risk of damaging the vessel walls during operation since they are more or less open circular apertures facing sideways out of the modular stent. When the operator then tries to navigate such a side branch vessel into place, as described above, the open apertures may tear or otherwise damage the delicate vessel wall when being moved around inside the vessel such that the vessel wall could rupture leading to internal bleeding. This should be avoided and improved covered stents, or (modular) covered stent systems, or implantation procedures for the two latter, would be advantageous.

The aforementioned alignment challenge makes that the operation time with hitherto known devices and medical procedures becomes often very long. Long operation times increase patient risk and potential problems related to such procedures. These problems include for instance increased risk for clots occurring during the operation. Also, long operation time implies long times of X-Ray use, which both the operator and the patient are exposed to. Moreover, contrast media is then used in large amounts.

It is therefore also desired to reduce the X-Ray dosage both for the patient and operator. Shorter scanning times or less positions scanned as well as reduced use of contrast agent that needs to be injected into the patient's blood is desired. There is therefore a need to reduce time needed for such implantation procedure, both for reduction of radiation exposure of primary radiation of the patient and secondary radiation (scattered radiation) of the operator. It would be advantageous to provide a covered stent, covered stent system, or procedure to facilitate a diminished scanning time. Examples of the invention described below provide this advantage as described below.

A further undesired issue with the known art is that implantation of a covered stent implant, in particular longer endoprosthesis systems of such covered stents covering multiple side branch vessels, is a complicated operation.

In known endoprosthesis the covered stents need to be assembled in a single deployment of the covered stent system. Should for instance side branch vessel openings of a main covered stent be positioned wrongly upon deployment in relation to the side vessel, re-positioning of the main (vessel) stent is very difficult or impossible. The prior art systems allow for no flexibility or very little tolerance upon deployment regarding mal-positioning of a main stent in relation to side vessels. Flexibility of reaching side vessels with such stent is desired.

Re-positioning of further parts of a stent graft system in relation to side vessels should be advantageously provided and the deployment procedure be facilitated. Hence, a novel covered stent, covered stent system or implantation procedure is desired to allow for individual positioning of one or more side vessel stent grafts. Examples of the invention described below provide this advantage as described in more detail below.

The minimal invasive implantation of an endoprosthesis requires continuous fluoroscopic scanning by X-Ray so that the operator can see where and how to position the different covered stent modules in a patient's vascular system for assembling the endoprosthesis inside the patient.

Frequent change of scan angles of the X-Ray modality is required to enable the operator to find branch vessels in three dimensions and the relation of covered stents to apertures of a covered stent module in a main vessel. The scan techniques used for this only enables the operator to see the scanned body in one plane at a time only, i.e. in two dimensions, one layer at a time.

Three dimensional visualization of branch vessels location and orifices in relation to apertures of a covered stent requires repeatedly moving a fluoroscopy scanner arm from one plane to another plane and then moving it back again to the first plane. This is needed to ensure alignment in three dimensions between the covered stent in the main vessel and the side branch vessel. It is important that the components are placed in a correct position at the implantation site in the patient.

With multiple apertures and side branch vessel connections to be aligned for one single covered stent in the main vessel, this task becomes particularly complicated.

There is therefore a need to make the assembly less complicated. The disclosure of examples of the invention found below advantageously provides a less complicated assembly of covered stents.

Thus, there is a need for a medical device and/or system, or medical procedures that are safer, avoiding the aforementioned drawbacks of known systems and procedures. Preferably a device and/or system or method is desired that makes the operation times shorter. Procedures are desired to be more easily performed by the operator. Simplified implantation procedure is desired. Complication rate is desired to be reduced. Novel medical procedures with reduced patient risk are desired. Simpler implantation is desired. Medical procedures are desired, which can be performed despite the fact that they would be avoided today in a risk assessment of patients. For instance as known stent systems would have implied too high risk for complications and open chest surgery is no option for many patients, in particular elderly patients), such simplified implantation, or devices facilitating simplified implantation, are desired. Hence, there is a desire to be able to provide novel medical procedures, implying reduced patient risk.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing medical devices, systems, and methods according to the appended patent claims.

The present novel covered stent system allows, amongst others, for individual, single delivery of side vessel stent branches. This reduces total operation time considerably. Also, patient safety is improved as time is reduced and/or other side vessels still are perfused when one side vessel stent is deployed by the operator.

The novel system allows for novel medical procedures, which today would imply too high risk for the patient. Thanks to the more simple implantation, medical procedures can be performed which were avoided today in a risk assessment of patients—for instance as known stent systems would have implied too high risk for complications and open chest surgery is no option for many patients, in particular elderly patients.

Examples of the invention described below allow advantageously reducing time for part of or an entire procedure. Implantation time is shortened compared to the prior art systems, and thus for instance the total dose is advantageously reduced. The angle of the x-ray modality needs to be changed less often than required by the prior art systems. Less amount of contrast medium is needed. Over all the below disclosure provides for reducing potential side effects for the patient. Moreover, the cost of the procedure will be reduced.

The covered stents discussed herein are in an example self-expanding, or in another example expandable by another device, such as an inflatable balloon.

According to a first aspect, a medical device is provided. The device is a covered stent comprising a main body, and at least one lateral side branch connected to the main body. The lateral side branch is flexible and expandable.

According to a second aspect, a system is provided.

The device and/or system may be used in medical procedures and methods as described herein.

Further examples of the disclosure are defined in the dependent claims, wherein features for the second and subsequent aspects of the disclosure are as for the first aspect mutatis mutandis.

Some examples of the disclosure provide for an improved navigation of and assembling of a covered stent or a plurality of covered stents, each in a side branch vessel from a main vessel.

Using this innovative system, device and/or method, an operation to position a covered stent with side branch connections, in particular with multiple side vessels (up to four side branches) such with for example three or four side branches, the time needed for implantation is expected to be considerably reduced, in the range of several hours less than conventionally would have been needed. Using conventional pre-fabricated stent grafts, such a procedure takes instead much longer time, around 10 hours operation time or longer. Despite the enormous reduction of surgery time for positioning the covered stent device/system, no safety of procedure is lost. Instead safety may be improved. The delivery of the innovative device and system is very reliable. Time for implantation is significantly reduced by the novel modular system and/or its components and/or the procedure for implantation possible by the system's features. This is described in detail below.

By covered stent means a stent having a liner, shell or being otherwise surrounded by a fabric or material. The covered stent can be partly or fully covered. A covered stent can also be a stent graft or endoprosthesis.

A side branch 3 may be laterally extendable and/or collapsible, i.e. expandable in a direction of a longitudinal axis along the side branch 3, which direction is preferably substantially perpendicular to a longitudinal axis along a main body 2 of a covered stent 1. Alternatively, or in addition, the side branch 3 may be expandable in a transverse direction, i.e. expandable transverse to the direction of an axis along the side branch 3. The side branch 3 may comprise a covered stent and may in some examples be a covered stent.

In examples, the side branch 3 is about 1 cm to 1.5 cm laterally extendable.

The side branch 3 is in an example integral with the main body 2, either by the covered stent of the main body 2 and the covered stent of the side branch 3 being integral, or by the cover of the main body 2 and the cover of the side branch 3 being integral. In an example both cover and covered stent of the main body 2 is integral with the cover and covered stent of the side branch 3. When the side branch 3 comprises the covered stent it is stiffer and can then resist more handling when e.g. deploying and/or re-deploying any further covered extension covered stent. This also allows for the side branch 3 to form a tighter connection with any further covered extension covered stent out from the side branch 3.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which

FIGS. 12A and 12B is a flow chart of an example of a medical procedure; and

FIG. 13 is a flow chart of an example of a method for navigating a covered stent to a branch vessel.

DESCRIPTION OF THE PREFERRED EMBODIMENTS

Figure 1:
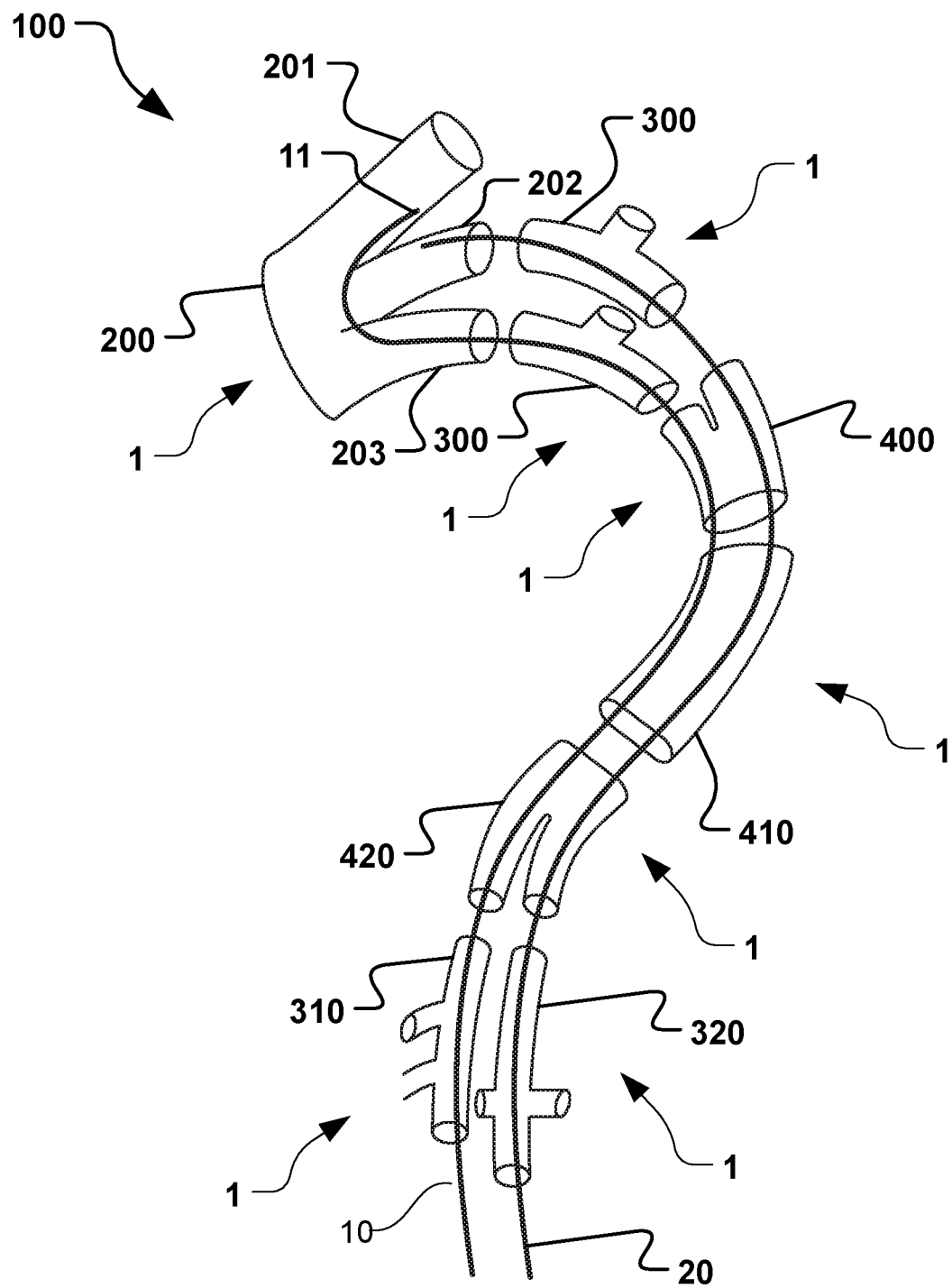
FIG. 1 is a schematic illustration that shows a system of different covered stent modules for implantation inside the aortic arch and thoracic aorta of a patient.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a medical device and in particular to a medical device for facilitating navigation of and assembling of a covered stent or a plurality of covered stents in communication with at least a side branch vessel. The implant can be used for treatment and/or repair of vascular disease, such as e.g. aneurysm. The example is illustrated with an arrangement in the aorta. The aorta may be structurally damaged of different reasons and need repair along at least a portion of the aorta 500. Sometimes extensive endoprosthesis are needed from the ascending aorta 501 via the aortic arch 502 down the descending aorta 503 and along the abdominal aorta 504 past the renal arteries 505.

Figure 2:
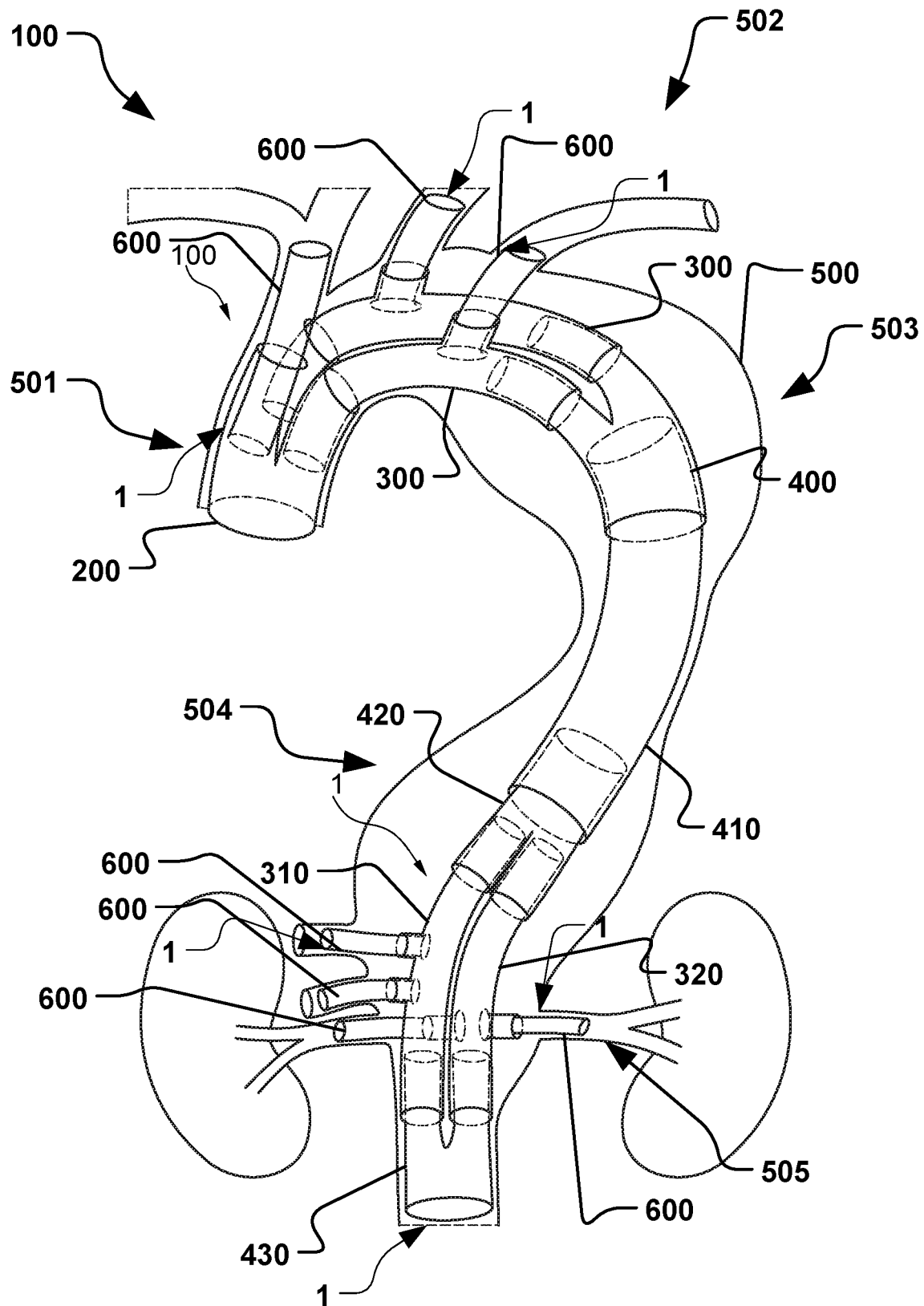
FIG. 2 is a schematic illustration that shows the system of FIG. 1 when it has been implanted inside the aorta of a patient.

An example of such an endoprosthesis including modular embodiments and assembly is illustrated in FIGS. 1 and 2 and the corresponding text herein. However, other anatomical structures may be provided for treatment with the devices and/or systems of the disclosure, including abdominal covered stents, peripheral stent grafts, endoluminal prosthesis, and include e.g. but not limited to peripheral veins, leg arteries, spinal vessels, neuro structures, lymphatic system, etc.

FIG. 1 shows a system of various covered stent modules 200, 300, 310, 320, 400, 410, 420, 430, 600 for implantation inside the aortic arch 502 and thoracic aorta 504 of a patient. FIG. 2 shows the system 100 of FIG. 1 when it has been implanted inside the aorta 500 of a patient and the modules being connected to each other. Further extension stent grafts 600 not shown in FIG. 1 are connected. A reliable communication of blood is provided through a main vessel, here the aorta 500, and into branch vessels, here neck vessel, renal arteries 505 and others. The aortic wall is in the example illustrated with weakenings/aneurysms in the descending aortic arch and abdominal aorta, needing treatment provided by the exemplary stent graft system 100.

In the illustrated example, a number of covered stents 1 (reference sign "1" cited together in this specification can be regarded a placeholder for "covered stent" or "covered stents," e.g. of the types disclosed herein, as for instance covered stents 200, 300, 310, 320, 400, 410, 600 etc.) is assembled and interconnected to fit inside parts of, or the entire, aorta of a patient to form a system 100. The covered stents 1 discussed herein may also be implantable in other target sites of the body for repairing and/or re-building conduits of vessels for liquid communication through the vessels.

FIG. 1 illustrates different kinds of modular covered stents 1 that can be used for an exemplary assembly of the system 100 of modular covered stents 1 that fit inside the vessels of and around the aortic arch 502 of a patient. The system 100 may be assembled in vivo or in vitro.

Alternatively, systems may include more or fewer covered stent modules. For instance, only the aortic arch may be covered by modules like covered stents 200, 300, 310, 320, 400, 410—all depending on the treatment site and treatment needs.

Some of the covered stents 1 have side branches 3 that are provided to extend blood communication through the system, and preferably into branch vessels. Examples of such covered stents are modular covered stents 300, 310, 320.

Some of the covered stents 1 have legs, i.e. the main body 2 of the covered stent 1 branches into two or more tubular parts. Examples of such covered stents are modular covered stents 200, 400, 410.

Alternatively, or in addition, and although not shown in the figures, a covered stent 1 may have both side branches 3 and legs. Other covered stents, not discussed or shown herein but commonly used today may also be used in the system 100.

The modular covered stent system 100 comprises a plurality of covered stents 1, wherein at least one of the covered stents is a covered stent 1. The plurality of covered stents 1 are configured to be inter-connectable to each other.

Alternatively, or in addition, the system further comprises an elongated navigation element 20, which allows the operator to navigate the covered stent and/or the side branch 3 of the covered stent 1 and align the side branch 3 with branch vessels. The elongated navigation element 20 is preferably a guide wire.

In an example, the covered stents have a substantially identical diameter at an inter-connection between two covered stents.

In an example, having the same diameter at an inter-connection means that the outer diameter at the inter-connection of one of the covered stents is substantially the same as the inner diameter at the inter-connection of the other covered stent, at least along a portion of the covered stent. The same diameter is maintained at least along an overlapping portion of the two covered stents, if overlapping. The two covered stents are thus for instance connectable by overlapping each other and one tube inside the other connected tube.

The stent structure of covered stents is part of the covered stent. It may have a pattern, like undulations. The pattern may be made by made by braiding, weaving, laser cutting of a tube, etc. The structure is a scaffold to support the structure outwards and provide a substantially tubular structure to ensure undisturbed blood flow through the tube when covered by a suitable liquid tight cover.

The undulations or pattern can be denser at the overlapping connection region than other regions of the covered stent—for a secure liquid tight connection of covered stent by improved mechanical strength.

The collapse of side branch 3 for delivery through a catheter may be obtained in multiple ways. It may be folded back, slid sideways along the catheter inner lumen, or compressed along its longitudinal axis. If a cover is provided (FIG. 9 etc.) the side branch, and covered stent, are collapsed and held inside the cover/restraining member 8. The restraining member may be of a material with low friction. Alternatively, or in addition, the inside of the catheter may be provided with a good sliding property material to facilitate movement of the covered stent along the inner lumen to the target site.

In another example having the same diameter means that the two covered stents to be connected have substantially the same inner diameter at the inter-connection and are connected in a non-overlapping manner, e.g. end to end connected. An additional inner liner may be provided at the connection site of the two covered stents.

In an example the two covered stents to be interconnected have both substantially the same inner diameter and substantially the same outer diameter at the interconnection, and the covered stents are connected by overlapping them when one of the covered stents is in a partially collapsed or folded state.

Having covered stents with the same or substantially the same diameter makes it easy for the operator to connect the various covered stents since the diameter of corresponding covered stent parts of the system 100 is similar and the operator does then not need to worry about any particular connection method, stent shape, connection site or the like. This means that the operator does only need to consider if the previous covered stent were a single, double, triple or further legged covered stent. This also makes the production of the covered stents easier since the diameter at the connection of the various covered stents are the same.

The overlapping region allows for length adaptation of the modular system. For instance the modular covered stents, 400, 410, 420 could be provided as a single integral unit. However, providing straight middle piece covered stent 410 separate from branched end piece covered stents 400, 420, allows for adjustment to specific patient anatomy (in the example different length of thoracic aorta). Overlap of the middle covered stent can be varied accordingly. Length adjustment of a system of modular covered stents is provided by an overlapping portion at openings of covered stents allowing for varying overlap and total length of the assembled modular system. This applies, mutatis mutandis to side vessel extension covered stents 600 connections, etc.

In the prior art, systems of covered stent modules are provided with covered stents that have a varying diameter in e.g. a tapered shape. They are connected by inserting a first folded tapered shaped covered stent into a second expanded tapered shaped covered stent.

When the first covered stent is expanded, the two covered stents form a connection. Such a system causes an unnecessary additional task for the operator to keep track of in addition to keeping track of all the covered stent modules not only being in the right order, in the right direction before and during the entire operation but also need to keep track of where and how these two cones fit to each other.

Providing the covered stents 1 with the same diameter gives the advantage that the operator can implant each covered stent 1 as explained above, or in an example in any direction he or she thinks is best. This will shorten the time required for assembling the system 100 and consequently the operation, drastically.

In an example, when the covered stent 1 has the same diameter as discussed above and is expanded or a side branch 3 or leg of the covered stent 1 is expanded, a flow through the covered stent 1 is more or less unchanged through it. Meaning that a liquid, such as blood, entering at one side e.g. the main body 2 will pass through the covered stent 1 and out through e.g. two legs at the other side and due to the expansion and same diameter of connection at the covered stents 1 an inlet and outlet area are substantially the same. This allows the operator to concentrate on connecting one covered stent 1 or part of a covered stent 1, such as a leg, at the time. The operator needs not to worry about the covered stent 1 disturbing the flow or throughput in the covered stent 1 or vessel.

Additionally, this allows for using a covered stent or a plurality of covered stents in a system and assemble at the implantation target site, i.e. not pre-manufactured for a specific patient. This is an advantage because over known systems. Known systems included hitherto pre-built, patient specific endoprosthesis. Usually, an image modality is used to scan the vessel system including the target site, e.g. a weakened aorta. The endoprosthesis is then manufactured based on the imaging data and delivered to the surgeon for implantation. This manufacturing of a patient specific endoprosthesis usually takes days to weeks, which is undesired. The anatomy of the vessel may change during this waiting time. The consequence may be that the manufactured endoprosthesis does not fit the patient anymore. Also, the waiting time is undesired as the patient mostly is in immediate need of the endoprosthesis, e.g. to avoid rupture of an aortic aneurysm. If desired, however, specific embodiments of the covered stents of the present disclosure may be manufactured patient specifically. A standard setup of different sizes readily available for implantation is preferred, though, as waiting time due to manufacturing is avoided.

The modular covered stent system 100 may further comprise a guiding element 10, like a suture or wire. Along guiding element 10 a delivery catheter may be threaded to the end of the guiding element 10. The guiding element 10 is distally affixed to a covered stent, for instance a suture may affixed by means of a knot, staple, weld, adhesive, or similar. See FIG. 3 or 8 for a more detailed described example.

Alternatively, or in addition, a guiding element 10 can be attached to the aorta of a patient at a desired target location.

Alternatively, or in addition, the attachment of a guiding element at its distal end may be releasable for removing the guiding element during the implantation procedure, as needed. A knot may be releasable, thermal detachment means provided, or the guide element be cut off.

However, the guiding element 10 is preferably left in place upon concluded implantation procedure. The guiding element 10 can be left in place after use. It may be made of a biodegradable material.

Figure 8:
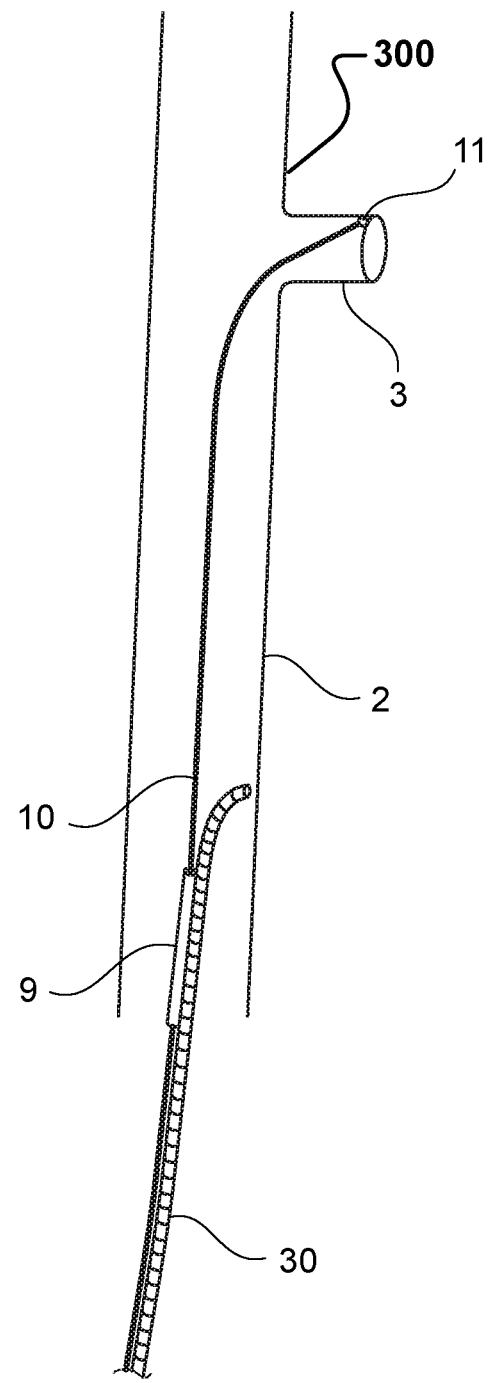
FIG. 8 is a schematic illustration of a covered stent with a side branch, and a catheter with a guiding mate for guiding the catheter for easy navigation of the side branch.

Along guiding element 10, the delivery catheter may be moved towards the distal end of the guiding element 20, e.g. by means of a guiding mate 9 on the catheter as described below (FIG. 8). Delivery of another element can then take place through this delivery catheter to a desired site at the distal end of the guiding element 10.

In this manner, a catheter can be moved along the guiding element to or towards the distal end thereof without fluoroscopic guidance. In this manner, reliability, and speed of delivery is improved while radiation exposure can be reduced.

In addition, the distal end of the guiding element 10 is for example arranged at a marker 21. The marker 21 is preferably arranged at a leg 4 of a covered stent for guiding delivery of another covered stent, e.g. as described below.

To make it easier to position another covered stent in relation to a leg of a first covered stent the marker 21 is provided at e.g. the leg of the first covered stent. In the same way a marker 21 may be provided on the side branch 3 of a covered stent 1, allowing easier aligning of the covered stent 1 in relation to a branch vessel.

The illustrated modular covered stent system 100 includes a first main vessel covered stent 200, 420 with a first upstream inlet branched into at least two downstream outlet branches.

Further it includes a covered stent that has a main body, and at least one lateral side branch connected to the main body. The lateral side branch is flexible and expandable. The covered stent is interconnectable to one of said downstream outlet branches and laterally connectable to a side stream vessel of said main vessel via said lateral side branch thereof. The at least two covered stents are thus sequentially interconnectable to one of said downstream outlets. In this manner, blood conduits are provided arranged in parallel by said at least two covered stents, one at a time assembled by the operator. The parallel blood conduits may be provided with one or more side branches each. Alternatively, or in addition, a blood conduit in form of a covered stent may be provided that has no lateral side branch, which then provides a straight blood flow path in parallel with e.g. a covered stent having one or more lateral side branches.

The modular covered stent system further includes a second main vessel covered stent 400, 430 with at least two upstream inlet branches collected in a downstream outlet. The inlet branches are interconnectable to a distal outlet of one of said two covered stents, e.g. covered stents 300, 310, 320 as shown in FIGS. 1 and 2.

Starting from the top of the system 100 as illustrated in FIGS. 1-2, there is illustrated a first covered stent 200 with three legs.

It should be noted that the covered stent modules are delivered in a specific order, starting with a three-legged covered stent 200 in the ascending aortic arch. Further covered stent modules are then delivered to the target site until the entire system is implanted. This is done in a very efficient and advantageous manner.

For instance, when the three legged covered stent 200 is deployed and implanted firstly of all modules in the ascending aortic arch. This can be done via a guide wire 21, e.g. in a femoral access approach. Further components can then be connected to the legs 200, 201, 202.

For instance a covered stent 600 can be delivered to the first leg 201 via a delivery catheter slid along guiding element 10, such as in the manner described with reference to FIG. 8. This covered stent can then extend blood flow into the first neck side vessel as shown in FIG. 2. The covered stent 600 is a covered stent without apertures for side vessels.

Delivery is thus provideable in two steps. Firstly, the side branch 3 is expanded. Then a side vessel covered stent 600 is deployed through the expanded side branch 3. Fixation of the side vessel covered stent 600 is done then. The entire prosthesis is flexible until the side branch is finally intubated, i.e. the side branch covered stent 60 is deployed and thus "locked" in position.

During delivery of covered stent 600, the two remaining legs 202, 203 are not obstructed and blood flow through the aortic arch is ensured during the implantation procedure.

The guiding element 10 is also running inside the third leg 203. This means, that over same guiding element 20 and delivery catheter over which the covered stent 600 was delivered, the covered stent 300 with a side branch is deliverable.

The initial guidewire 21 for delivering the three-legged covered stent 200 to its target site, is used for delivering and connecting a covered stent 300 to the second leg 202.

The location of three-legged covered stent 200 is preferably marked with a fiducial marker 21 that can be seen during imaging by e.g. MRI, CT or X-ray.

As the guiding element 20 extends out from the first leg 201, all three legs can be located and modular covered stents interconnected at the orifices of the three legs.

The guiding elements 10 are for guiding subsequent covered stents along them so that the subsequent covered stents can be connected to a previously implanted covered stent.

In addition, or alternatively a navigation element 20, such as a guide wire, is used instead for or together with one or more guiding element(s) 10 in the system 100 for guiding all or almost all of the covered stents of the system 100 to their target site.

Next, the system 100 includes in proximal direction, downstream the aorta, two covered stents 300 with one side branch each, positioned in the aortic arch 502 upon implantation. The two covered stents 300 are each guided by one of the first and second guiding elements 10, respectively. These modular covered stents 300 are described in more detail below, e.g. with reference to FIGS. 5A, 6, 7, 8, 10 and 11. Each of covered stents 300 is distally connected to a leg of the three legged covered stent 200. The side branch exit is expandable, and in liquid communication with a neck vessel when expanded. A further covered stent 600 is further connected with its proximal end, respectively, extending into the remaining two neck vessels respectively (see FIG. 2). Delivery of these further covered stents 600 can be done fiducial marker guided (not shown), with guidewires and contrast medium feedback, and/or a guiding element 10 can be connected to the branch (see FIG. 8) facilitating delivery of the further covered stents 600 through the orifice of the side branch of covered stent 300 and into the respectively neck vessel.

Delivery of each covered stent 300 and extension is done sequentially. While delivering the first of these two units, the other leg of three-legged stent 200 is not obstructed and blood flow through the aorta ensured. Also, when delivering the extension into a neck vessel, blood flow both downstream the aorta and into the neck vessel is uninterrupted during the procedure.

When both covered stents 300 are interconnected and delivered, a parallel flow through the aorta is provided with sufficient blood flow needed due to a high ratio of lumen diameter to (healthy) aorta diameter.

Then, downstream the aorta there is proximally a covered stent 400 with two distal legs united into a single lumen body having a proximal orifice. The first leg of covered stent 400 is delivered running along guiding element 10 for interconnection with the proximal orifice of the covered stent 300, which in turn is previously distally interconnected to the third leg 203 of the distally and upstream in the aorta arranged and previously implanted covered stents 300. The other distal leg of covered stent 400 is delivered along guidewire 20. It is distally interconnected to the proximal orifice of the other covered stent 300, which in turn is previously distally interconnected to the second leg 202 of the distally and upstream in the aorta.

A further covered stent 410, without side branches or legs is distally interconnected to the proximal orifice of covered stent 400. The further covered stent 410 is delivered over both the guiding element 10 and guidewire 20 which both are run inside this covered stent 410. In case the covered stents 300 include one or more guiding element(s) 10, previously used for the extension covered stents into the neck vessels, these one or more guiding element(s) 10 will also be run through the lumen of covered stent 410.

Next in downstream aorta direction is a two-legged covered stent 420 branching the blood flow into two proximal legs from a distal common lumen and orifice interconnectable to proximal orifice of the distal covered stent 410 previously implanted. Guiding element 10 runs inside the first leg. Guidewire 20 runs inside the other leg. The two legged stent is delivered over the two latter in a delivery catheter, which may be the same as used for delivery of previously distally delivered modules.

And finally, at the bottom of the drawing, two covered stents 310, 320 are illustrated, with two side branches 3 each. These two covered stents 310, 320 are described in more detail below with reference to FIGS. 5A and 5B respectively.

The first covered stent 310 is delivered by means of guide element 10. A further delivery catheter may be used for this purpose, such as described with reference to FIG. 8 with the difference that the guide element runs all the way through the first covered stent 310. A further guide element may be attached to one or more of the side branches of the first covered stent 310 for delivery of extension covered stents 600 extending into side vessels, see FIG. 2 when implanted.

The second covered stent 320 is delivered by means of guidewire 20. The delivery catheter is again used for this purpose, such as described above. A further guide element may be attached to one or more of the side branches of the second covered stent 320 for delivery of extension covered stents 600 extending into side vessels, see FIG. 2 when implanted.

The proximal end of the two covered stents 310, 320 are interconnected to two distal legs of a two legged covered stent 430.

As described above, the system 100 is thus positioned as shown in FIG. 2.

In an example a method of interconnecting a plurality of covered stents is provided which can be performed either in vivo and/or in vitro.

In an example, before assembly, and/or during assembly, the covered stents of the system 100 are sorted and placed in the correct order for assembly. In an example, and if assembled during implantation, a number of catheters 30 may be used as described.

Although not shown in FIG. 1, further navigation elements 20 and/or guiding elements 10 may be provided for navigation of the side branches 3 and aligning of the side branches 3 with branch vessels, as explained. To make it easier to see which navigation element 20 or guide element 10 that goes to a certain covered stent, leg or side branch, each navigation element and guide element is labelled in an example.

Modular covered stents, as described with the system 100 will now be described in more detail. As mentioned above, the modular stents maybe arranged differently in other systems than the one illustrated in the figures. Some modular covered stents may be provided individually for connection to known units, or individually, depending on the target site, treatment need and/or patient history.

Figure 3:
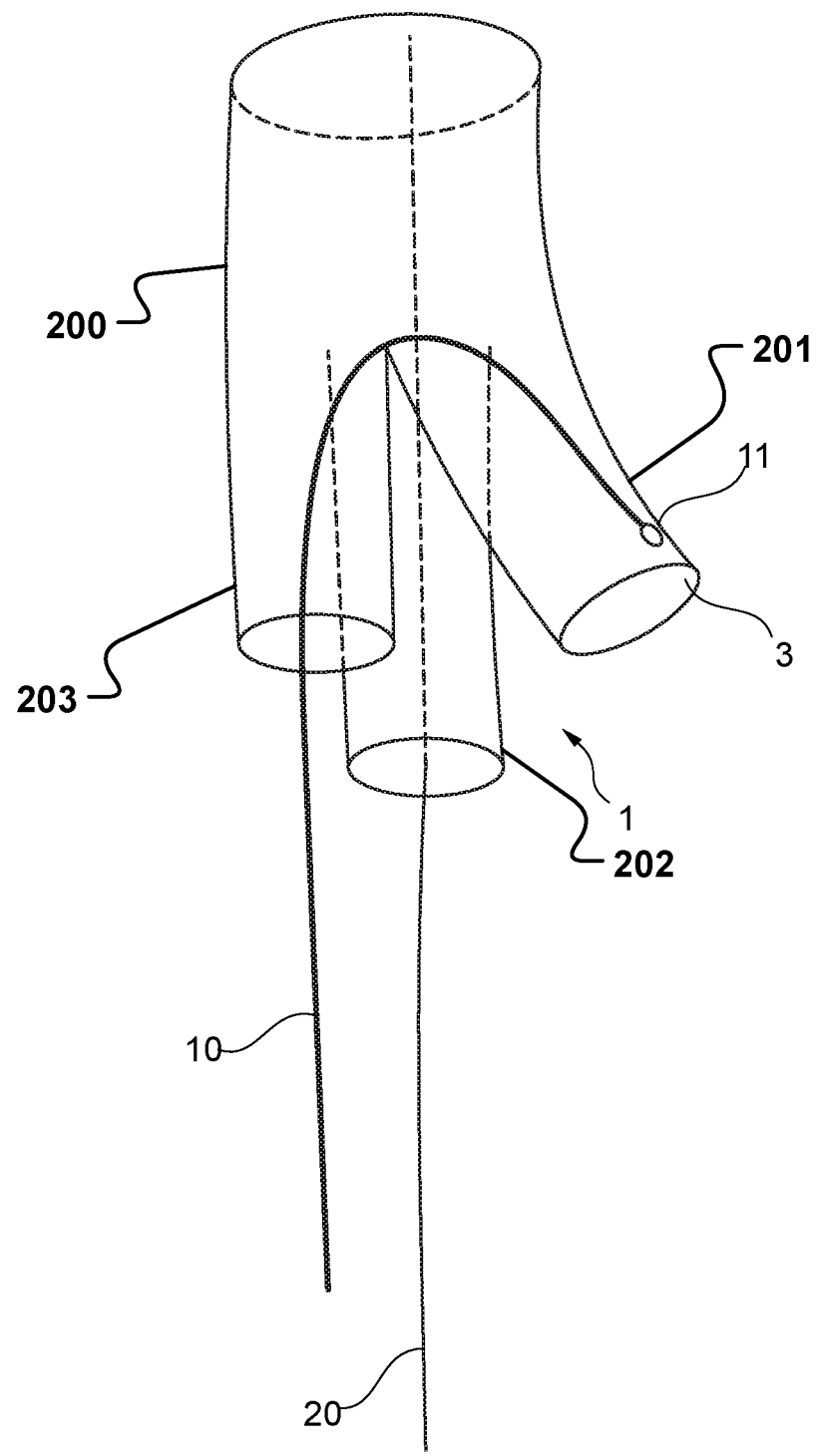
FIG. 3 is a schematic illustration of a covered stent with three legs, and a navigation element and a suture for easy navigation to all three legs.

FIG. 3 illustrates a covered stent 200 with three legs 201, 202, 203, and a navigation element 20 and guiding element 10 in from of a suture for easy navigation to all three legs. FIGS. 3 and 8 illustrate examples of how one or more (one shown) guiding element 10, such as a suture, may run through a covered stent during implantation of a system 100 of covered stents.

The three legs 201, 202, 203 are provided for connection to three aortic arch side vessels: one into the neck artery, and two through channels (when assembled) with side branch vessel connection. The three legs 201, 202, 203 may have different lumen diameter and length.

The pre-attached guiding element 10 extending into one leg (203) and into another leg (201) allows for a direct intubation of a side vessel. Direct access is provided to all side branches of the prosthesis without the difficulty of locating the side branches with the open legs of such an implant. This has hitherto been difficult to navigate, due to the length of the delivery catheter where the operator usually has no feeling for targeting to a side vessel. Also the pulsating blood flow during the procedure, and other procedural difficulties of intubation of side branches, are less relevant than for known covered stent. 3D to 2D visualization difficulties are avoided, less x-ray dosage is needed, the procedure is provided with significant time reduction, and reduced patient risk.

The guiding element 10 is used for guiding further covered stents to a connection location so that the covered stents can be connected together into to the system 100 of covered stents. More about FIG. 8 can be found below.

In an example as illustrated in FIG. 3, the navigation element 20, here a guide wire 20 runs inside and through the three legged covered stent 200 via a leg 202. During implantation of the system 100, the navigation element 20 is inserted far enough into the vessel so that any covered stent can follow the navigation element 20 to a desired target site location.

In an example, the covered stents are guided to their respective position by sliding them along a navigation element 20 inside a delivery catheter. Upon release out of the distal catheter end, the covered stents are expanded into place and implanted at that target site.

FIG. 3 further illustrates that one or more guide elements 10, such as sutures, may be attached to the covered stent 200. In the figure, the suture 10 is attached inside the second leg 4 and extends out through the third leg. The guiding elements 10 have, as discussed above, a similar purpose to the purpose of the navigation element 20 of guiding delivery catheters for delivery of covered stents such that they can be connected to form the system of covered stents 100.

The operator can easily locate the two legs and navigate further covered stents to any of the two legs. The operator can via the guiding element 10 navigate a first further covered stent 600 to the leg 201 where the guiding element 10 is attached. When the first further covered stent 600 is correctly positioned and connected to the three-legged covered stent 200, the operator can, via the same suture 10, navigate a second further covered stent to the leg 203 where the suture exits proximally from the three legged covered stent 200. The navigation element 20 ensures that the operator can locate also the third leg, as shown in FIG. 3, and deliver units that way as desired.

Generally, one advantage of using the guiding element 10, such a suture, instead of the navigation element 20, such as a guidewire, is that a suture or a wire is provided flexible and can be bent and manipulated as desired without breaking. The navigation element 20 is usually stiffer such that it can exert a distal force from the operator for e.g. pushing along a vessel from a puncture site. A catheter is then thread over the guide wire and moved along the guide wire. The guide wire may then be removed from the catheter for delivery of a unit through the catheter.

The flexible characteristics of the guiding element 10 allows for e.g. the covered stent to be placed into positions and/or navigated around e.g. corners in the covered stent and/or in a vessel and/or side branch 3, which the guiding element 20 cannot. The guiding element runs outside of a delivery catheter through which a unit is deliverable.

As explained previously in relation to guiding element 10, the position 11 where the distal end of the guiding element 10 is attached to the covered stent is advantageously provided with a marker, so that it can easily be seen during scanning by e.g. MRI, CT or X-ray.

Figure 4:
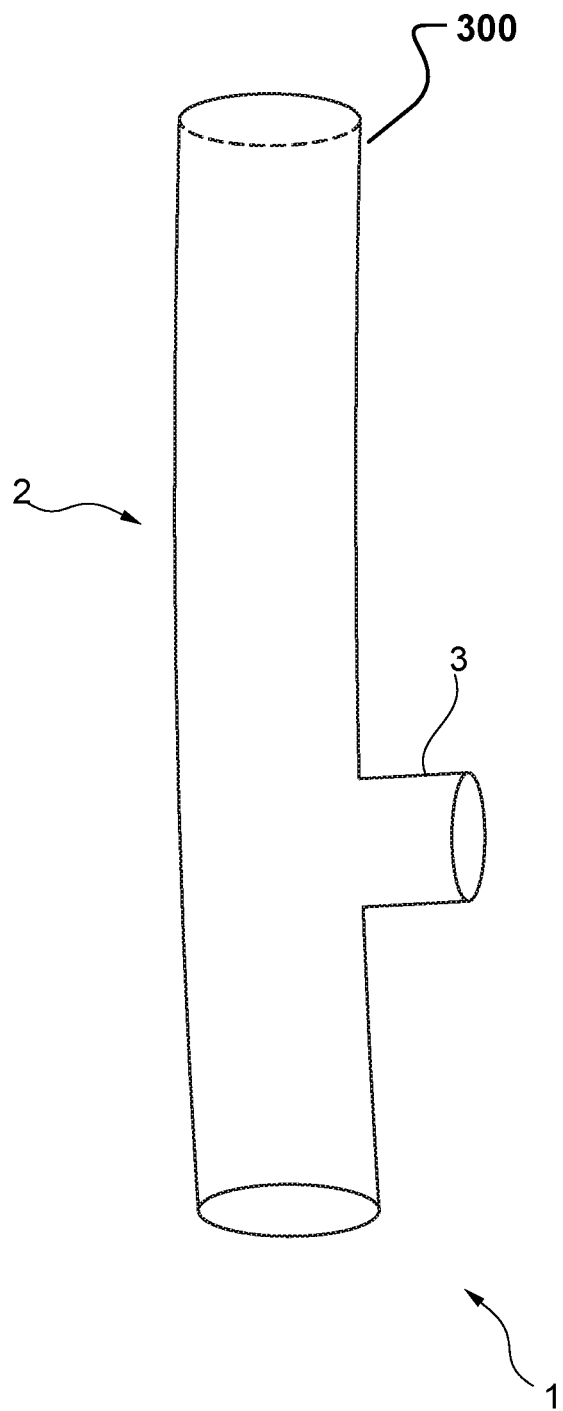
FIG. 4 is a schematic illustration of a covered stent with a side branch.

FIG. 4 illustrates a covered stent 1 with a side branch and is an example a covered stent 300 with a side branch 3 of the exemplary system 100 (FIGS. 1 and 2).

The covered stent 1 has a main body 2, which is a covered stent, and a lateral side branch 3 connected to the main body 2. The side branch 3 protrudes out from the main body 2 and is flexible and expandable. One advantage of the side branch 3 being flexible and expandable is that the side branch 3 is easily movable in at least one dimension independent of the movement of the main body 2 such that a branch vessel can be found and more easily aligned with during implantation to enter into with the side branch 3.

Figures 5A, 5B:
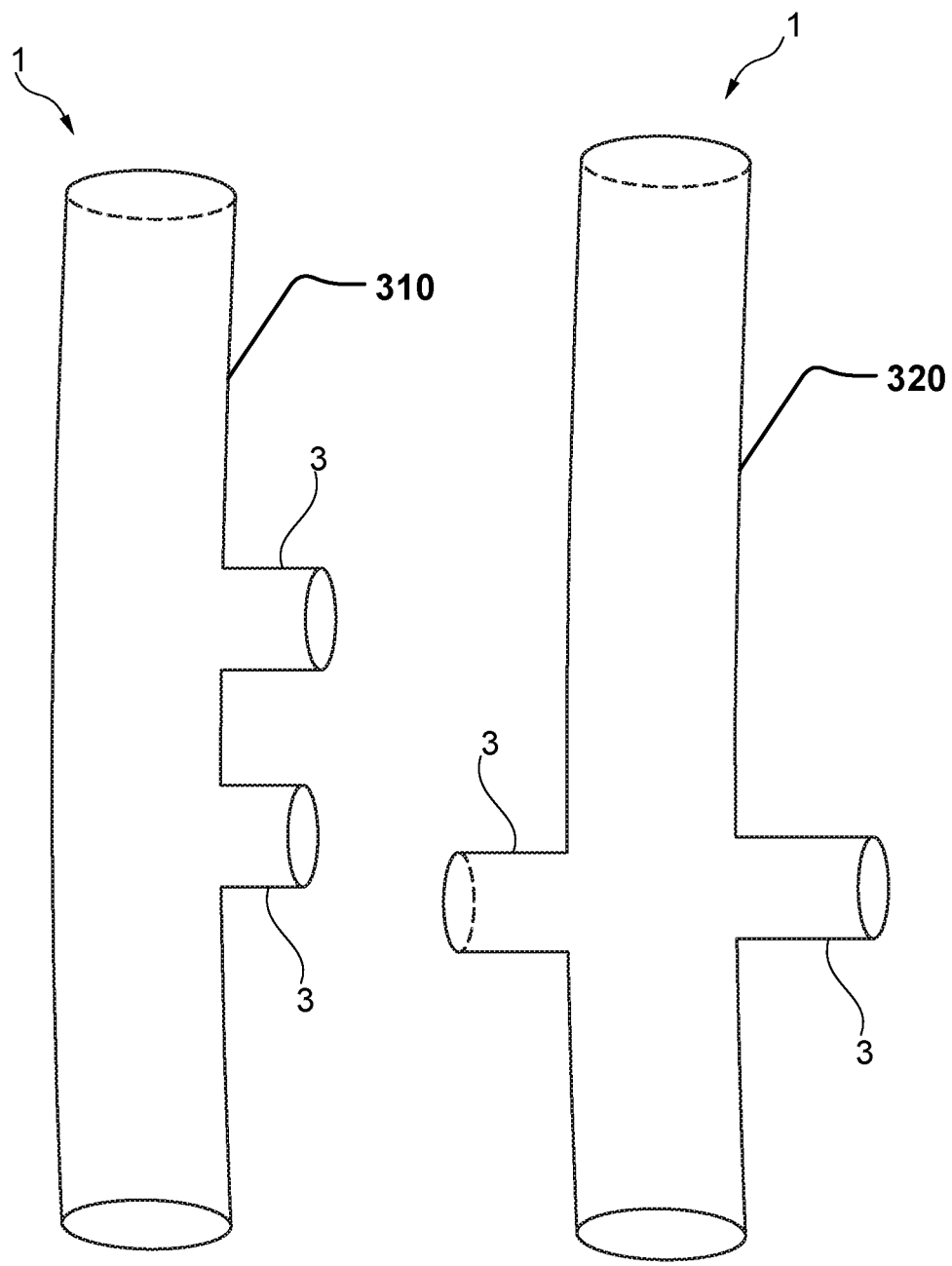
FIGS. 5A and 5B are schematic illustrations of two examples of a covered stent with more than one side branch.

Alternatively, or in addition, the covered stent 1 may have more than one side branches 3, like covered stents 310, 320 shown in FIGS. 5A and 5B.

Alternatively, or in addition, the covered stent 1 has a plurality of legs and wherein at least one of the legs comprises a side branch 3. Thus, in an example (not shown) the covered stent 1 has a plurality of legs and each leg comprises a side branch 3. In an example the side branch 3 is deflated, collapsed or folded and may look like the side branch 3 of FIG. 3. Collapsed may include radially and/or longitudinally collapsed states.

Figure 7:
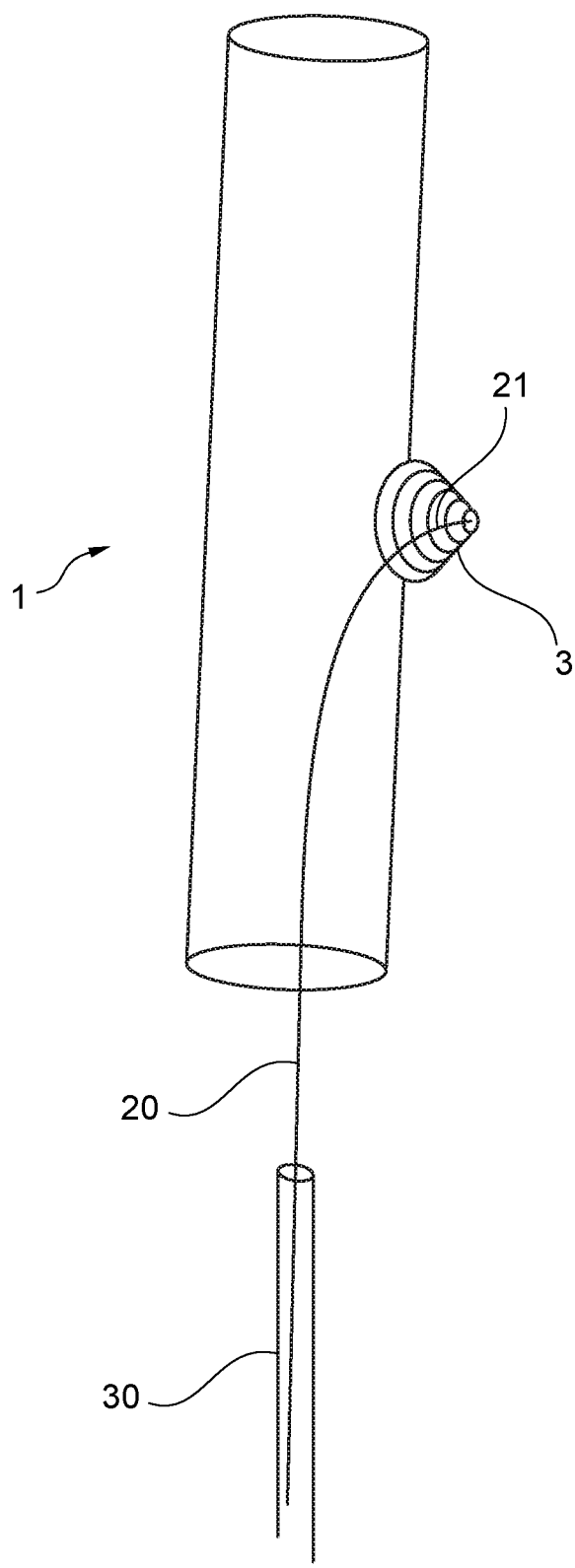
FIG. 7 is a schematic illustration of a covered stent with a folded or collapsed side branch be used to locate a branch vessel.

In an example the shape of the side branch 3 when collapsed may be dome shaped, or substantially half sphere shaped, see FIG. 7 for a non-limiting example. This allows the covered stent 1 to be safer for insertion during operation and/or navigation to a branch vessel than known devices of today since the side branch 3 does not have any sharp edges that can tear, rip or penetrate the branch vessel as known devices of today. However, the branch vessel 3 is preferably only longitudinally expandable and cylindrical in shape, as e.g. shown in FIG. 1, 2, 4, 5A, 5B, 6, 8.

Figure 6:
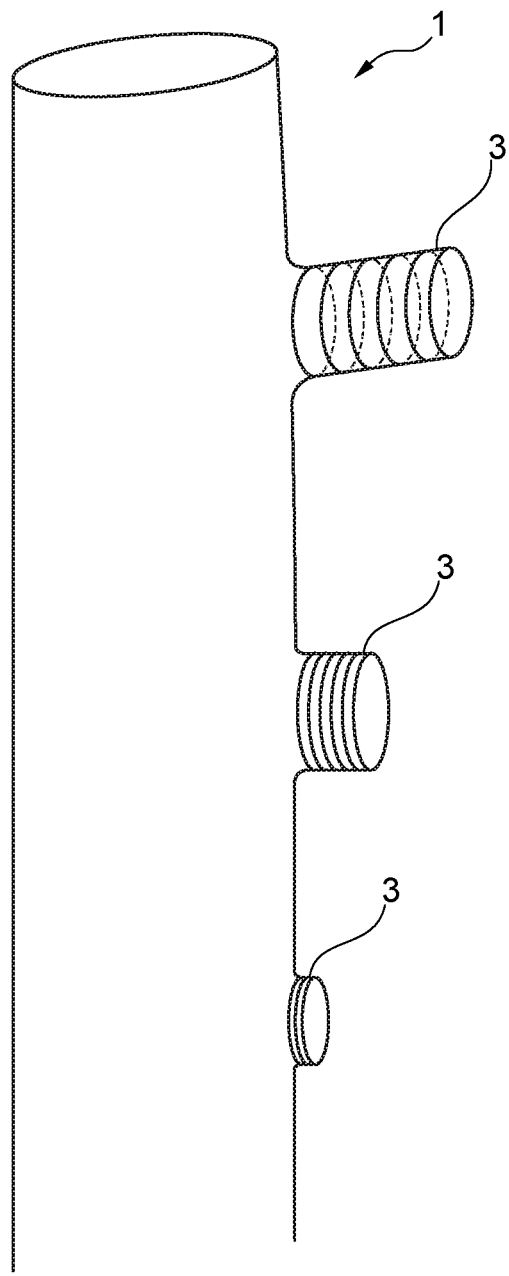
FIG. 6 is a schematic illustration of, bottom-top, one example of a side branch which is self-expandable from a collapsed to an expanded shape.

The side branch 3 is configured so that its shape may be changed to fit the branch vessel and allows for further extension away from the main body of the covered stent into the branch vessel with for example another covered stent or covered stent. Such expanded state includes in particular a longitudinally expanded shape of the branch 3, such as schematically illustrated in FIGS. 4, 5A, 5B, 9 and 10. Transition from the longitudinally collapsed state to the expanded state may be done by unfolding, stretching, spring effect or other similar operations of the branch 3, as illustrated in FIG. 6.

FIGS. 5A-b show two examples of a covered stent with more than one side branch in the expanded state. The covered stent 310 shown in FIG. 5A has two lateral side branches 3 protruding from the same side. The covered stent 320 in FIG. 5B also has two side branches 3, but they protrude from opposite sides.

Other configurations of side branches are provided as needed for anatomical reasons at a target site. In an example, the side branches 3 are distributed at any desired location on the main body 2. In an example the locations are based on the layout of the vessel wherein the covered stent 1 is going to be placed, and its side vessels. Although not shown, the covered stent 1 may also have more than two side branches 3.

As will be explained more, further below, the lateral side branch 3 may be expandable from a first protruding length or size to a second protruding length or size. This expansion may be independent of an expansion of the main body 2, or vice versa, the expansion of the main body 2 may be independent of the expansion of the side branch 3. This means that when the covered stent 1 with the side branch 3 is collapsed or folded, in one example the side branch 3 can be expanded or unfolded without the main body 2 of the covered stent 1 being expanded or unfolded. In another example the main body 2 of the covered stent 1 can be expanded or unfolded without the side branch 3 being expanded or unfolded.

As the side branch portion 3 of the covered stent 1 is flexible when extended, alignment with the side branch vessel is less critical than with conventional covered stents. Thanks to the flexibility, navigation towards and/or into the side branch vessel is facilitated during implantation and when implanted by the flexibility of the side branch 3, illustrated in e.g. FIGS. 7 and 11. Some misalignment of the orifice of the side branch 3 at the main body of the covered stent 1 in relation to the branch vessel orifice may be corrected by the path of the flexible laterally extending side branch 3. A blood communication path of the side branch 3 can be extended by matingly engaging a further covered stent or covered stent graft interconnecting at the distal end of side branch 3 and extending into the side branch vessel.

FIG. 6 shows an illustration, bottom-top, of an example of a side branch which is self-expandable from a collapsed to an expanded shape. FIG. 6 illustrates one example of a covered stent 1. The covered stents discussed herein are in an example self-expanding, or in another example expandable by another device, such as an inflatable balloon.

The covered stent 1 has a main body 2, which is a covered stent, and a lateral side branch 3 connected to the main body 2. The side branch 3 protrudes out from the main body 2 and is flexible and expandable. One advantage of the side branch 3 being flexible and expandable is that the side branch 3 is easily movable in at least one dimension independent of the movement of the main body 2 such that a branch vessel can be found and more easily aligned with during implantation to enter into with the side branch 3.

In an example the covered stent 1 may have more than one side branch 3. In an example the covered stent 1 has a plurality of legs and wherein at least one of the legs comprises the side branch 3. Thus, in an example the covered stent 1 has a plurality of legs and each leg comprises a side branch 3. In an example the side branch 3 is deflated, collapsed or folded and may look like the side branch 3 of FIG. 7. Collapsed may include radially and/or longitudinally collapsed states.

In an example the shape of the side branch 3 when collapsed is dome shaped, or substantially half sphere shaped. The above allows the covered stent 1 to be much safer for insertion during operation and/or navigation to a branch vessel than known devices of today since the side branch 3 does not have any sharp edges that can tear, rip or penetrate the branch vessel as known devices of today.

The side branch 3 is configured so that its shape may be changed to fit the branch vessel and allows for further extension away from the main body of the covered stent into the branch vessel with for example another covered stent or covered stent. Such expanded state includes in particular a longitudinally expanded shape of the branch 3, such as schematically illustrated in FIGS. 4, 5A, 5B, 9 and 10. Transition from the longitudinally collapsed state to the expanded state may be done by unfolding, stretching, spring effect or other similar operations of the branch 3, as illustrated in FIG. 10.

In an example expansion may be obtained by a spring effect of the covered stent 1 and/or the side branch 3, as e.g. illustrated in FIG. 10. The expansion may come to an equilibrium position within the vessel in an example.

The lateral side branch 3 is preferably integrally formed with the main body. The side branch is in some embodiments provided with a spring elastically self expanding the side branch 3 in the longitudinal direction of the side branch 3 without radial expansion. The spring may be a helical spring wound as shown in the Figure.

The covered stent 1 or side branch 3 may include wires that are suitably arranged. In an example the wires may have a U shape in a longitudinal direction of the covered stent. In another example the wires may be helically wound, as illustrated in FIG. 10. In yet other examples they may be arranged in suitable patterns, like zigzag patterns etc.

In an example the wires may be wires interwoven with the covering. The wires may form a mesh, like a knitted pattern or a braiding. The wires may also be laser cut to form the springy pattern.

Alternatively, or in addition, the wires or other expansile components of the present device may be made of a shape memory material. The shape memory effect of such wires may provide for a change of shape, such as collapsed to expanded shape, by means of known triggers like temperature. Suitable materials include Nitinol, CrMo alloys, shape memory polymers, etc.

When the covered stent 1 is exiting a delivery catheter, it will resiliently expand out from the main body of the covered stent, as for instance described below with reference to FIG. 10.

FIG. 7 illustrates how a covered stent with a folded or collapsed side branch can be used to find a branch vessel. The volcano shape of side branch 3, is as mentioned above only an example. A guide wire 20 is fed through the side branch and a catheter is thread over the guidewire. Then a delivery passage through the side branch is provided.

FIG. 8 illustrates a covered stent with a side branch, and a catheter with a guiding mate for guiding the catheter for easy navigation of the side branch.

In an example, illustrated in FIG. 8 the catheter 30 comprises a guiding mate 9 which is configured to run over the guiding element 10 and/or navigation element 20 when guided by the guiding/navigation element to the side branch 3.

In this example the guiding mate 9 is a length of tube attached to the catheter 30. Alternatively, the guiding mate 9 is integrally formed with the catheter, e.g. by suitable extrusion of the tubular member of the catheter. The guiding mate may be formed as an inner lumen, and/or integrated with the catheter wall. The guiding mate 9 may be integral with the catheter, or alternatively a separate element suitably attached to the guiding element 10, e.g. by adhesion, welding, or other mechanical attachment means.

Alternatively, or in addition, the guiding mate 9 comprises a ring, eyelet, snarl, or loop for threading through of the guiding element 10. An inner diameter of the guiding mate 9 is matched to receive an outer diameter of the guiding element 10 with some tolerance to avoid too much friction between the two elements for sliding motion along each other.

The guiding mate 9 is a unit for matingly receiving the guiding element 10 therethrough for being slidingly movable along the guiding mate 9 to and from the guiding mate's distal end where it is attached to a covered stent. The guiding element 10 is configured to be threaded through the guiding mate 9 for being slidingly moveable along the guiding mate 9. Threading through of the guiding element 10 is suitably done outside of the patient at the proximal end of the guiding mate, e.g. a suture, thread, filament or wire, of e.g. multifilament strands, that are for instance braided together, to form a flexible guiding unit 10.

Alternatively, or in addition, the guiding mate 9 can be a lumen of a dual (or multi) lumen catheter or any other suitable element which is configured to allow sliding on the guiding element 10 and preferably does not damage the vessel or lumen it is used in.

The guiding mate 9 has advantageously a distal end or opening which is arranged a suitable length remote, i.e. proximal, of the distal end of the catheter 30. In this manner, the distal end or opening of the catheter 30 may advance further distally than the guiding mate 9 when at the end position of the guiding element 10 and/or navigation element 20, e.g. at a fixation point, such as a knot of a suture, where the guiding element 10 and/or navigation element 20 is distally affixed to a covered stent, e.g. at an orifice or opening thereof as described and illustrated herein.

The guiding mate 9 has thus a distal end or opening which preferably is arranged at the catheter proximal (at a distance) of a distal end or distal opening of the catheter 30.

In this manner, it is ensured that the distal end of catheter 30 for instance enters a side branch into which a delivery is to be made through the lumen of the catheter, e.g. a covered stent into a side vessel and assembly as well as interconnection with a main vessel covered stent in which the fixation point is located. In this manner, the side vessel covered stent can be delivered to the right location, i.e. branch opening, of the main vessel covered stent with minimal X-ray dosis as no 3D visualization is needed for the operator.

In an example, also related to FIG. 8, a guiding element 10 is attached to the side branch 3. This allows any further elements to be implanted, preferably covered stents, to be easily delivered through a catheter 30 with guiding mate 9 for e.g. being connected to the side branch 3 or delivered out of a side branch 3 with minimal effort and improved reliability as well as patient safety.

As shown in FIG. 8, the guiding mate 9 is in some embodiments placed at a distance from the distal end of the catheter 30. One advantage with the guiding mate 9 at a distance from the distal end of the catheter 30 is that the catheter 30 may then reach further than the position 11 of the attachment of the guiding element 10. E.g. if the guiding element 10 is attached at the side branch 3, the catheter can reach further out through the side branch 3. This enables easy access for positioning and connecting e.g. an extension covered stent at the side branch 3.

The distal end portion of the catheter 30, preferably distally of the guiding mate 9 distal end, can additionally, or alternatively, be bent, see FIG. 8. This allows for a desired exit angle of the orifice of the delivery catheter 30 at its distal end, for instance substantially perpendicular in relation to a longitudinal axis of a main body (300).

However, the guiding mate 9 distal portion or end may in some embodiments reach all the way up to the distal end of catheter 30. Improved, advantageous minimally invasive delivery of elements through a side branch is ensured in any case.

Figure 9A:
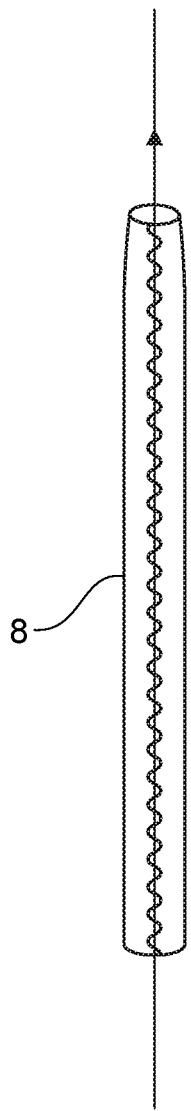
FIGS. 9A-9C is a schematic illustration of a restraining member and a covered stent being self-expandable from a collapsed to an expanded shape by removal of the restraining member.

In an example, as illustrated in e.g. FIGS. 9A,b,c, 10A-10C and 11A-11B, the covered stent 1 is provided with a restraining member 8 that prevents the covered stent 1 from expanding until release of the restraining member provides for controllably expanding the covered stent 1.

In an example the restraining member 8 is made of a Gore-Tex material, e.g. a flat sheet, fabric or nonwoven material. Alternatively, any other suitable biocompatible materials may be chosen for the restraining member that can be inserted into the body and easily manipulated as well as protect any vessel or lumen from the covered stent 1 during deployment.

Figure 9B:
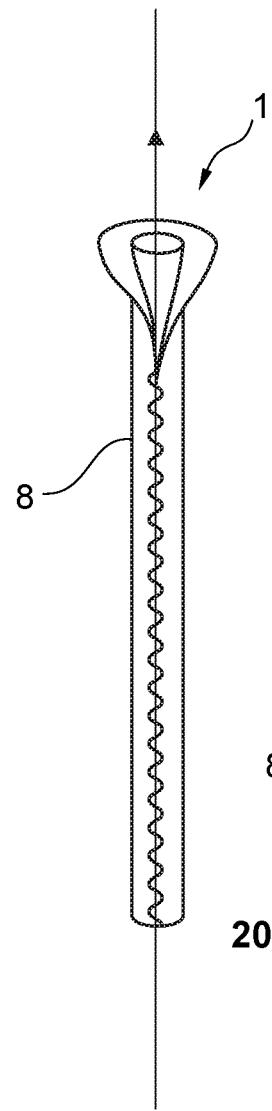
Figure 9C:
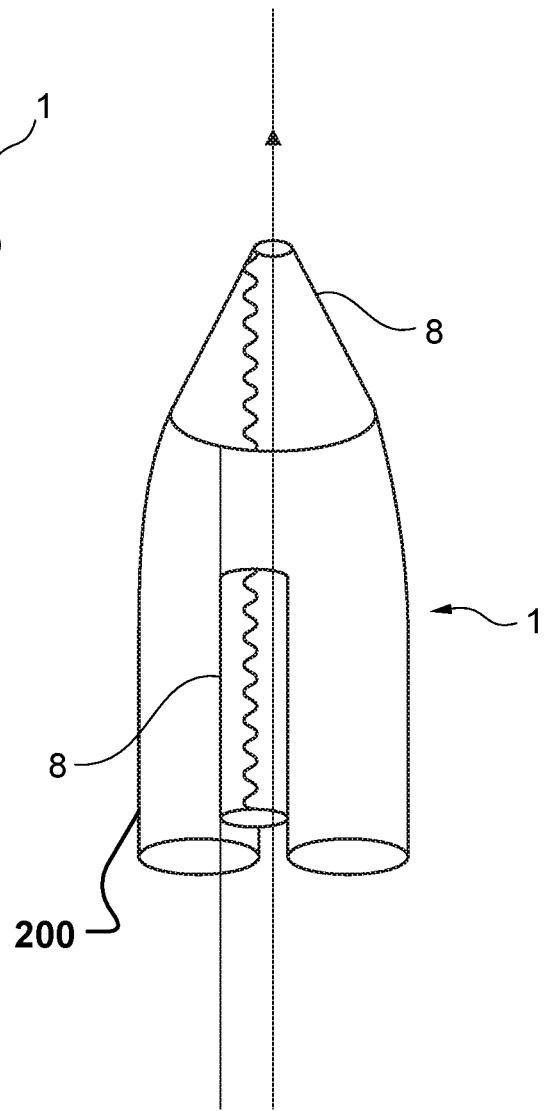

FIG. 9A-c illustrate an example of a restraining member. For instance a covered stent 200 that is self-expandable may be provided with such restraining member 8. The covered stent transitions controllably from a collapsed to an expanded shape by removal of the restraining member.

In an example, the removal of the restraining member 8 is done by simply pulling on a string which then releases a seam holding together a sheet of the restraining member 9 arranged around the covered stent. Pulling the release string unfolds the restraining member along the seam, depending on the distance pulled on the string. The restraining member unfolds thus partially or fully, as for instance illustrated in FIGS. 9A-c. In an example more than one string/seam is used to select where the restraining member 8 is removed from restraining the covered stent and/or side branch 3.

Alternatively, or in addition, the restraining member 8 is configured to be partially removable so that the expansion of the covered stent 1 and/or side branch 3 can be selected individually. This is illustrated in FIG. 9A, where the covered stent is fully restrained by the restraining member 8. In FIG. 9B the restraining member 8 is shown as partly opened and thereby allowing the covered stent to partially expand. Partially expanded stent may still be repositioned if so desired.

The example illustrated in FIG. 9C shows more than one restraining member 8 for restraining portions of a covered stent. Each restraining member is thus provided for restraining different parts of a covered stent, here in the example the three-legged covered stent 200. In This way, the three legs can easily be expanded individually, one at a time or simultaneously. In the same manner a covered stent 1 with a side branch 3 can be partially or fully expanded by releasing it from e.g. a restraining member around the main body 2 and another restraining member 8 around the side branch 3.

The collapsed unit (FIG. 9A) is introduced to a target site through a delivery catheter that may have a guiding mate 9 slidable along a guiding element 10 as described above. The assembly shown in FIG. 9 (and similar others) may include one or more guiding mate(s) 10 itself, as e.g. shown in FIG. 3. The latter guiding element(s) 10 are led outside from inside the restraining member 8 from the covered stent (here 200), and further proximally towards the proximal end of the catheter, outside the patient. Thus further elements may be delivered through the covered stent when implanted, as described herein.

In an example the removal of the restraining member 8 is done by simply pulling on a string which then unfolds the restraining member partially or fully, as in e.g. FIGS. 9A-c. In an example more than one string is used to select where the restraining member 8 is removed from the covered stent 1 and/or side branch 3.

Alternatively, or in addition, the string of the seam of the restraining member is one of guiding element(s) 10 when attached to the covered stent 200. The guiding element then 10 is attached distally to the covered stent, as e.g. in FIG. 3, runs proximally out of an orifice of the covered stent 200. Then it is folded back, runs inside the protection unit 8. Turning back proximally again, it provides the releasable seam. When pulled and removed from the seam, i.e. the restraining member is released, it is further pulled back, leaving a guiding element 10 for use as a catheter guide. This synergetic guiding element 10 and seam of a protective unit/restraining member 8 is advantageous in that the number of components is reduced that needs to be drawn outside of the patient, amongst other advantages. The restraining member 8 is configured to be partially removable so that the expansion of the covered stent 1 and/or side branch 3 can be selected individually. This is illustrated in FIG. 9A, where the covered stent 200 is fully restrained by the restraining member 8. In FIG. 9B the restraining member 8 is partly opened and thereby allowing the covered stent 200 to have partially expanded, here along its length.

Another example is illustrated in FIG. 9C, where more than one restraining member 8 is used to restrain different parts of the three-legged covered stent. In this manner, for instance one or more of the three legs of covered stent 200 can easily be expanded individually, one at a time or simultaneously. In the same manner a covered stent 1 with a side branch 3 can be partially or fully expanded by releasing it from e.g. a restraining member around the main body 2 and another restraining member 8 around the side branch 3 (not shown)

Figure 10A:
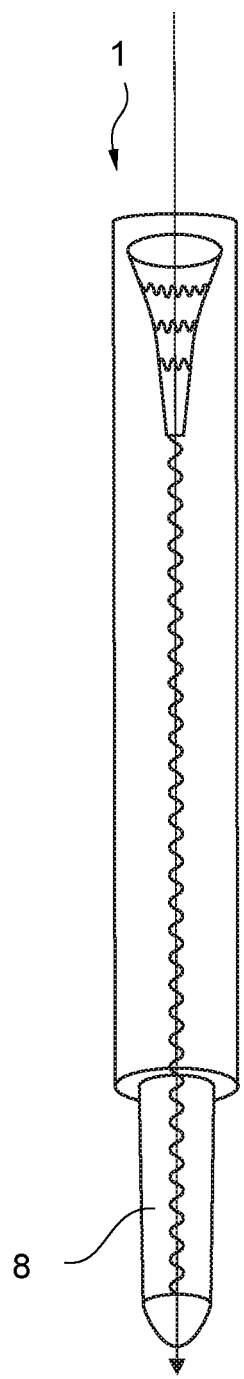
FIGS. 10A-10C is a schematic illustration of a sheath used to hold the covered stent in a collapsed or folded manner, and to controllably release the covered stent, partially or fully.
Figure 10B:
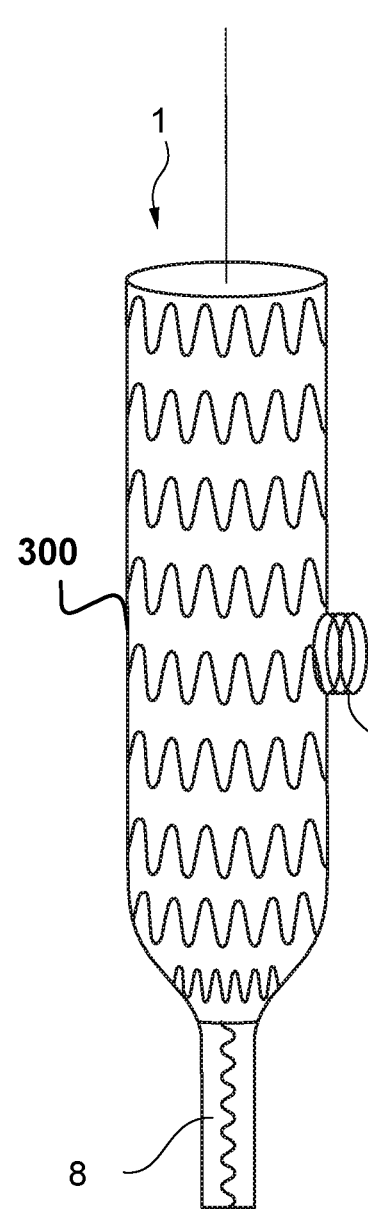
Figure 10C:
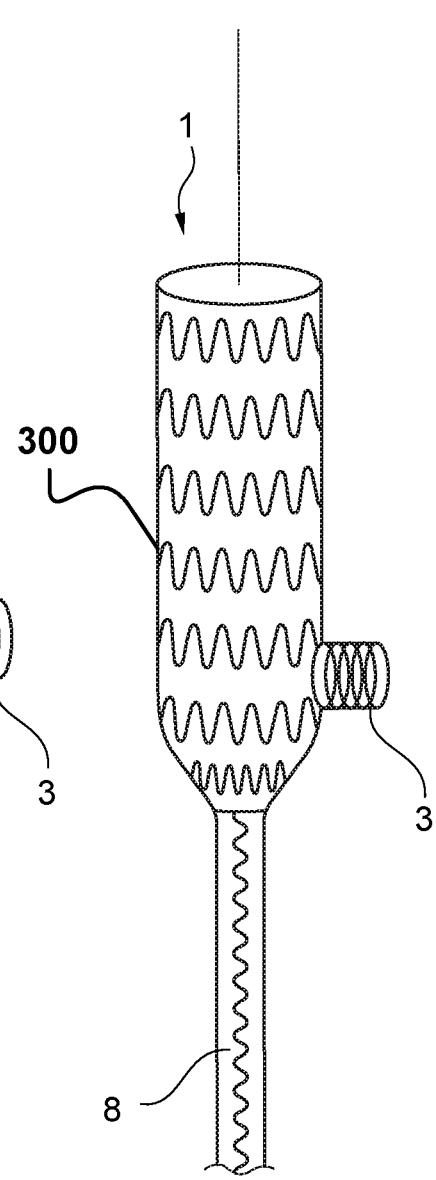

FIGS. 10A-10C illustrate how a sheath may be used to hold the covered stent in a collapsed or folded manner, and to controllably release the covered stent, partially or fully.

FIG. 10A illustrates how the covered stent 1 is first released from restraining member 8 from one side, the right hand side as shown in the top part (a) of FIG. 10. As illustrated in the middle and bottom parts (b and c) of FIGS. 10B and 10C, the part of the covered stent 1 that comprises the side branch 3 is then released. This is further illustrated in FIGS. 11A and 11B, where the covered stent 300 is partly released from the restraining member 8 to allow easy fitting of the side branch 3 with a branch vessel. When the part of the covered stent 300 that comprises the side branch 3 is released from the restraining member 8, the side branch 3 is aligned with the branch vessel and is then expanded into the branch vessel. The covered stent 300 is then fully released from the restraining member 8, as illustrated in the bottom part of FIG. 11B. A covered stent 600 extending further into the side vessel is shown delivered and deployed as described herein.

Figure 11A:
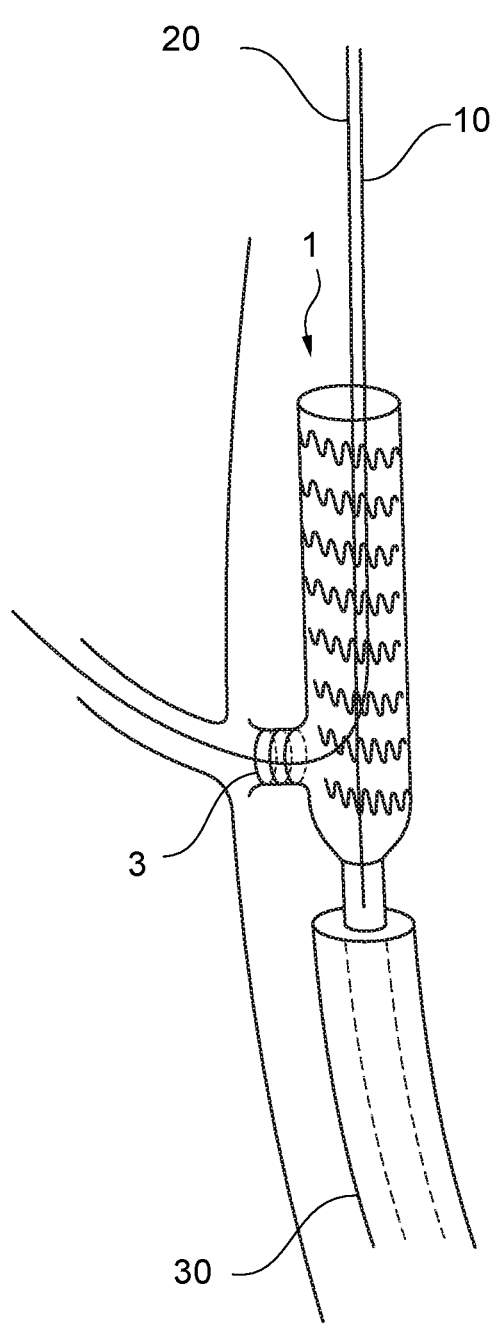
FIGS. 11A and 11B is a schematic illustration of a covered stent before and after the covered stent is fully expanded.
Figure 11B:
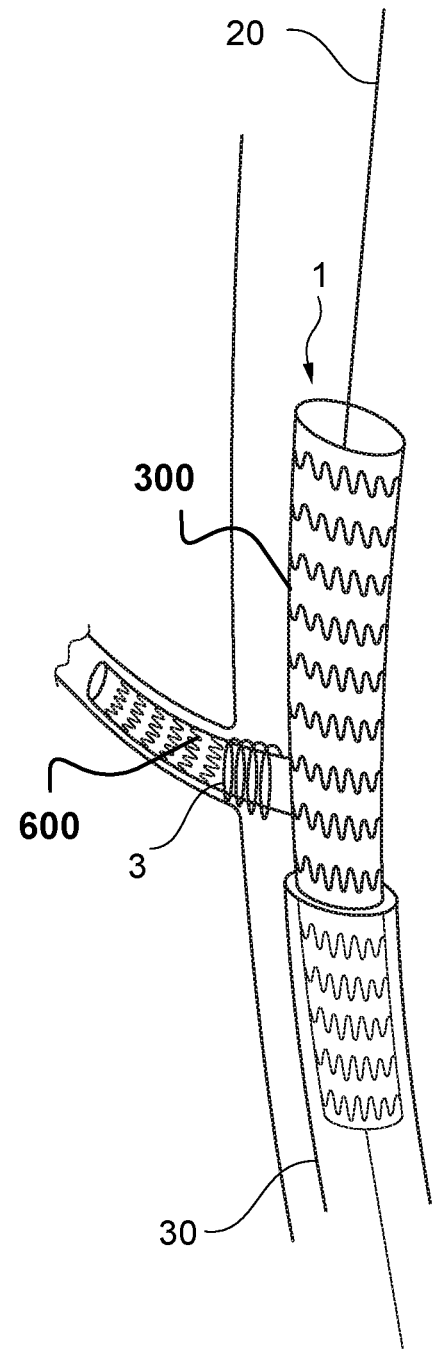

FIGS. 11A and 11B illustrate an example of a covered stent 1 which can be used in an easy method of finding a branch vessel. The covered stent 300 is pushed fully out of a delivery device 30, such as a catheter, and the main body 2 of the covered stent 1 is expanded.

The side branch 3 is in examples expanded by pushing it outwards and/or configured to expand by itself, as disclosed above and illustrated in e.g. FIGS. 6, 7 and 9.

A further pushing element (not shown) can used to push the flexible side branch 3 in a desired direction and outwards, so that it expands from a folded or collapsed state. This applied in case the side branch 3 is not self-expandable.

In case of a self-expandable side branch 3, it will expand radially outwards from the main body as soon as it is released from the delivery catheter (30), and/or a restraining unit 8 is removed.

For easier alignment with a branch vessel, the covered stent side branch 3 can be provided with a marker 21, as e.g. illustrated in FIG. 3. The marker 21 will make it visible to the operator when the side branch 3 is level or aligned with a branch vessel. By having only one marker at the side branch 3 it will be easier for the operator to align the covered stent 1 to its desired location by use of an imaging device, such as X-ray, than today's covered stents having a plurality of markers that need to be brought in alignment in fluoroscopy. The marker 21 is in examples any fiducial marker visible under common type if imaging devices used in healthcare or covered stent placement such as MRI, X-ray, Ultrasound, and so on. Covered stent structures usually are themselves difficult to see under e.g. fluoroscopy. Markers may e.g. made of gold or similar materials allowing good visibility in such imaging.

In an example, the side branch 3 is folded or collapsed and restrained by a guide element 10, such as a suture 10. The guiding element 10 is for instance wrapped around the side branch 3, and is releasable connected on the inside of the side branch 3 or otherwise attached to the side branch 3 causing it to be releasably folded or collapsed. Pulling the guiding element proximally then releases the side branch 3 from the collapsed state to the expanded state. Guiding element 10 remains in place for use as a catheter guide.

In an example the covered stent 1 is aligned with a branch vessel by moving the main body 2 of the covered stent 1, as e.g. illustrated in FIGS. 9-11. In an example, this is achieved by the covered stent 1 only being partially pushed out of the catheter 30 and/or partially freed from the restraining device 8 as also disclosed above, so that the covered stent 1 can be moved by moving the catheter 30, or otherwise moved by e.g. a pusher wire, e.g. illustrated in FIGS. 9 and 10. Preferably, the side branch 3 is self-expandable.

In an example, the covered stent 1 is moved upwards until the marker 21 on the side branch 3 aligns with the branch vessel. Then the covered stent 1 is rotated until the side branch 3 enters the branch vessel. When the side branch 3 has entered the branch vessel the guiding element/e.g. suture 10 is released, allowing the side branch 3 to expand into the branch vessel, either by itself or by pushing it outwards.

In a further alternative example, the covered stent 1 is aligned with a branch vessel by navigating both the main body 2 of the covered stent 1 and by navigating the side branch 3 of the covered stent 1.

FIGS. 12A-12B show flow charts of two examples of a medical procedure.

The method 700 comprises the steps of accessing 710A target site being a vessel in a patient; delivering 720 a first covered stent to the inside of the vessel at the target site through a delivery catheter, wherein the target site has a side branch vessel; delivering 730 a second covered stent to said first covered stent; connecting 740 said first covered stent to said second covered stent for providing a blood flow to said side branch vessel. The delivery of said second covered stent includes sliding a catheter along a guiding element 10 to a position inside a lumen of a side branch of said first covered stent; and expanding said second covered stent for connecting to said first covered stent.

Alternatively, or in addition, the method 800 is provided. The second covered stent may have a side branch 3. The method includes delivering a second covered stent to a side vessel through a side branch 3 of said first covered stent. The method 800 comprises the steps of accessing 810 a target site being a vessel in a patient; delivering 820 a first covered stent to the inside of the vessel at the target site through a delivery catheter, wherein the target site has a side branch vessel; expanding 830 said side branch 3, delivering 840 a second covered stent to said first covered stent and through said side branch 3 to said side vessel; connecting 850 said first covered stent to said second covered stent for providing a blood flow to said side branch vessel.

In a specific example the method includes delivering and assembling the system 100 as explained above and with a final layout illustrated in FIGS. 1 and 2.

The method starts in the example with soft guidewire being inserted into a vessel of a patient. Using a soft guidewire ensures that no part of the vessel is damaged during insertion. Further, the soft guidewire 10 can be bent and thereby be navigated through the vessel system of the patient to a target site.

Then, a first catheter 30 is inserted, over the soft guidewire, into the vessel of the patient and navigated until it reaches the target site. Guided by the catheter 30, a stiffer navigation element 20 is then inserted into the catheter and thus vessel of the patient.

The target site in the example is the ascending aorta where the three legged covered stent 200 is then positioned via the delivery catheter in the aortic arch. The delivered state, assembled with further components in the aortic arch is illustrated in FIG. 2.

As explained above other target sites in the body could also be chosen as an alternative.

Then a three-legged covered stent 200 is collapsed or folded to fit inside the first catheter 30 and pushed along it with the navigation element/guide wire 20 may running inside the main part of the covered stent and extending out through one of the legs 201.

The three-legged covered stent 200 is provided with a guiding element 10 attached inside one of the other legs, as described above. In an example a location near or to the left of the aortic arch is preferred.

Each guide element 10 and navigation element 20 can be labelled at the end proximal end for easy identification. The labelled end is configured to be outside of the patient during implantation.

Following, when at the correct position of the target site, the covered stent 200 is pushed out of the catheter 30 and allowed to fully or partially expand or unfold, as discussed above. It is rotated until the legs match the main vessel and the neck branch vessels of the aorta. And as explained above this alignment can be performed in various ways.

Next, when the three legged covered stent 200 is in place, the system 100 can easily be built up with further modules. As discussed above this can be done in several ways and in this example two covered stents 1 having side branches 3 and covered stents 600 for extending into the branch vessel are deployed following the three-legged covered stent 200 as described above with reference to FIGS. 1 and 2.

In the example illustrated in FIGS. 1 and 2 the extension covered stent 600 is navigated via the guide element 10 attached inside one of the legs of the three-legged covered stent 200 and navigated through the three-legged covered stent 200 and positioned so that it can extend out through the leg. Here the covered stent 200 is expanded and connected to the leg in an overlapping manner.

Following, the first covered stent 300 with the side branch 3 is slid into place along the guide element 10 and connected to the third leg 203. After or before the deployment along the guide element 10 the second covered stent 300 is slid along the guidewire 20 and connected to the second leg 202.

When delivering a covered stent the side branch(es) 3 are at the same time navigated into place with the covered stent and expanded into, or at least towards the branch vessel. Following, any additional extension covered stent can be inserted based on the desired need to further extend into the branch vessel.

Next, a covered stent 400 with two legs is moved in a collapsed state inside the first catheter 30 along guide wire 20 and guide element 10. The covered stent 400 is oriented so that the legs are positioned towards the covered stents 300 already connected. Each leg is guided along one of the guide element 10 and the guide wire 20, so that each leg can be guided to one of the previous covered stents 300 with side branches 3. When in place, the covered stent 1 is released from the catheter 30 and allowed to expand.

Next a tubular shaped covered stent 410, without legs or side branches, is pushed into place through the catheter 30, and navigated and connected to the previous covered stent 400 in a similar manner but now having both the guiding element 10 and the guide wire 20 running inside.

Then a two-legged covered stent 420 is connected to the tubular shaped covered stent 1 in the same manner. This two-legged covered stent 420 is oriented with the legs away from the covered stents already distally connected upstream the aorta. These legs run along the guiding element 10 and the guide wire 20, respectively.

After connection of the two-legged covered stent 420, a covered stent 310 with two side branches 3 is guided along the guiding element 10 through a delivery catheter, in a manner similar to previously delivered covered stents. When the main body of the covered stent is in approximately the right place, further navigation of the side branch 3 is done to be rotationally correctly oriented towards the side vessels. The side branches 3 are thus aligned with the branch vessels and expanded into the branch vessels. Distally, the covered stent 310 is connected with one of the legs of the two-legged covered stent 420.

Then, a covered stent 320 with two side branches 3, and further guiding 10 or navigation elements 20, is guided via the catheter 30, aligned with branch vessels and connected to the second leg of the two-legged covered stent 420.

Finally, a last two-legged covered stent 430 is positioned and the two legs are connected to the two covered stents 310, 320 with two side branches 3, in a similar manner as described above, by use of a delivery catheter 30 and running along the guiding element 10 and the guide wire 20, respectively.

When the system 100 is connected and complete, all remaining navigation elements 20 and catheters 30 are removed from the patient. Guide elements 10 may be distally cut and remaining length left in place, preferably for subsequent biodegradation.

In an example, illustrated in FIG. 2, a complete system 100 is shown assembled and implanted inside an aortic arch of a patient. As can be seen, the different covered stents 1 have been connected to each other and side branches 3 have been extended into branch vessels and further extended with covered stents 1.

FIG. 13 illustrates a method for navigating a covered stent 1 to a branch vessel. The method 900 comprises the steps of providing 910 the covered stent 1, as discussed above, and navigating 920 the lateral side branch 3 into a branch vessel by moving the lateral side branch 3.

In an example this is performed by using an elongated navigation element 20, as also discussed above. In one example it is performed using a guide element 10 and a catheter 30 with a guiding mate 9, as described in relation to FIG. 8.

The method may further comprise the step of expanding the lateral side branch 3 from a collapsed state into the branch vessel when navigated to the desired position at the branch vessel. As described in relation to e.g. FIGS. 9-11, this may be done by navigating the covered stent 1 so that the side branch 3 is aligned with a branch vessel, then expanding the side branch 3 into the branch vessel, and finally expanding the rest of the covered stent 1.

In an example the method further comprises the step of interconnecting an expansion element at the lateral side branch 3 and into the branch vessel for further extension into the branch vessel. The expansion element may be a covered stent 1.

EXAMPLES OF METHODS AND PROCEDURES

17. A method for navigating a covered stent to a branch vessel, comprising the steps of:
providing a covered stent according to examples (as e.g. in appended claims 1-8),
navigating the lateral side branch into or towards a branch vessel by moving the lateral side branch using a guide element (10).

18. The method for navigating a covered stent to a branch vessel according to example 17, comprising the step of expanding a covered stent delivered through the lateral side branch from a collapsed state into the branch vessel when navigated in position at the branch vessel.

19 The method for navigating a covered stent to a branch vessel according to example 18, comprising the step of interconnecting an expansion element at the lateral side branch and into the branch vessel for further extension into the branch vessel.

20. The method for navigating a covered stent to a branch vessel according to example 19, wherein the expansion element is a covered stent.

21. A method of interconnecting a plurality of covered stents comprising the step of:
providing a covered stent comprising a bendable guiding element (10) connected at an exit of a side branch.

22. The method of interconnecting a plurality of covered stents according to example 21 comprising sliding a catheter by means of a guiding mate (9) along the guiding element to the exit of the side branch and delivering another covered stent through said catheter along the bendable guiding element for interconnection of covered stents and wherein the covered stents have a same dimension at the interconnection.

23. A medical procedure comprising accessing (710) a target site being a vessel in a patient; delivering (720) a first covered stent to the inside of the vessel at the target site through a delivery catheter, wherein the target site has a side branch vessel; delivering (730) a second covered stent to said first covered stent; connecting (740) said first covered stent to said second covered stent for providing a blood flow to said side branch vessel, wherein the delivery of said second covered stent includes sliding a catheter along a guiding element 10 to a position inside a lumen of a side branch of said first covered stent; and expanding said second covered stent for connecting to said first covered stent.

24. A medical procedure comprising accessing (810) a target site being a vessel in a patient; delivering (820) a first covered stent to the inside of the vessel at the target site through a delivery catheter, wherein the target site has a side branch vessel; expanding (830) said side branch (3); delivering (840) a second covered stent to said first covered stent and through said side branch (3) to said side vessel; connecting (850) said first covered stent to said second covered stent for providing a blood flow to said side branch vessel.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A covered stent comprising:
    a main body,
    at least one lateral side branch, connected to the main body, and
    a guiding element consisting essentially of a flexible and bendable suture or wire having a first end configured to be left in place upon concluding an implantation procedure within a patient and directly fixed to a terminal end portion of said at least one lateral side branch, and a second end attached to a delivery catheter, wherein said guiding element is configured to navigate a subsequent covered stent through said delivery catheter to connect said subsequent covered stent to said at least one lateral side branch of said main body, wherein said first end of said suture or wire remains affixed to said terminal end of said at least one lateral side branch after said subsequent covered stent is connected.

2. The covered stent according to claim 1, wherein the at least one lateral side branch is laterally extendable and/or collapsible from or towards the main body.

3. The covered stent according to any previous claim, wherein the at least one lateral side branch comprises a covered stent.

4. The covered stent according to claim 3, wherein the at least one lateral side branch is integral with the main body, and a spring elastically self expanding in the longitudinal direction of the side branch without radial expansion.

5. The covered stent according to claim 1, wherein a cover of the at least one lateral side branch and a cover of the main body are integral.

6. The covered stent according to claim 1, wherein a covered stent structure of the at least one lateral side branch and a covered stent structure of the main body are integral.

7. The covered stent according to claim 1, wherein the at least one lateral side branch has a first protruding length or size and is expandable to a second protruding length or size.

8. The covered stent according to claim 1, wherein the main body and the lateral side branch are expandable, and the at least one lateral side branch is expandable independently of an expansion of the main body, or vice versa.

9. A method for navigating a covered stent to a branch vessel, comprising the steps of:
    providing a covered stent according to claim 1,
    navigating the at least one lateral side branch into or towards a branch vessel by moving the lateral side branch using a guide element.

10. The method for navigating a covered stent to a branch vessel according to claim 9, comprising the step of expanding a subsequent covered stent delivered through the at least one lateral side branch from a collapsed state into the branch vessel when navigated in position at the branch vessel.

11. The method for navigating a covered stent to a branch vessel according to claim 9, comprising the step of interconnecting an expansion element at the at least one lateral side branch and into the branch vessel for further extension into the branch vessel.

12. The method for navigating a covered stent to a branch vessel according to claim 11, wherein the expansion element is a subsequent covered stent.

13. A modular covered stent system comprising,
    a plurality of covered stents, wherein at least one of the covered stents comprising:
    a main body,
    at least one lateral side branch, connected to the main body, wherein each lateral side branch is flexible and expandable, and
    a first end of a guiding element is configured to be left in place after a procedure and directly fixed to a terminal end portion of said at least one lateral side branch, and a second end of a guiding element is attached to a delivery catheter, wherein said guiding element is configured to navigate a subsequent covered stent through said delivery catheter to connect said subsequent covered stent to said at least one lateral side branch of said main body, wherein said first end of said guiding element remains affixed to said terminal end of said at least one lateral side branch after said subsequent covered stent is connected,
    wherein the plurality of covered stents are configured to be inter-connectable to each other and the guiding element consists essentially of a flexible and bendable suture or wire.

14. The modular covered stent system according to claim 13 further including said delivery catheter having a guiding mate.

15. The modular covered stent system according to claim 14, wherein the guiding mate has a distal end or opening which is arranged at the catheter proximal of a distal end or distal opening of the catheter.

16. The modular covered stent system according to claim 13, further comprising an elongated navigation element, and wherein the elongated navigation element is extending into the at least one of the covered stents from the outside of the at least one of the covered stents and arranged at the lateral side branch for moving the lateral side branch in a desired direction.

17. The modular covered stent system according to claim 13, wherein the covered stents have a same diameter at an inter-connection between two covered stents for mating engagement of the two covered stents at the inter-connection.

18. The modular covered stent system according to claim 13, further comprising at least a marker at a first covered stent of said plurality of covered stents, and the guiding element arranged at said marker for guiding another covered stent of said system different than said first covered stent.

19. The modular coved stent system according to claim 13, wherein said plurality of covered stents includes a first main vessel stent with a first upstream inlet branched into at least two downstream outlet branches, and
  wherein said first main vessel covered stent is proximally connected to said downstream outlet branches and laterally connectable to a side stream vessel of said main vessel,
  wherein at least two of the plurality of covered stents are sequentially interconnectable to said two downstream outlet branches for providing blood conduits arranged in parallel by said at least two covered stents.

20. The modular covered stent system according to claim 19 including a second main vessel covered stent with at least two upstream inlet branches collected in a downstream outlet, one of said inlet branches interconnectable to a distal outlet of one of said at least two covered stents.

21. A method of interconnecting a plurality of covered stents comprising the steps of:
  providing a covered stent comprising a bendable guiding element connected at a first side with an exit of a side branch and at a second side to a delivery catheter,
  navigating a subsequent covered stent through said delivery catheter and along said guiding element, and
  connecting said subsequent covered stent to said side branch of a main body of said covered stent,
  wherein said guiding element consists essentially of a flexible and bendable suture or wire and is affixed to a terminal end of said side branch exit at a fixation point thereof and said suture or wire remains affixed to said terminal end of said side branch after said subsequent covered stent is connected.

22. The method of interconnecting a plurality of covered stents according to claim 21 comprising sliding said delivery catheter by means of a guiding mate along the guiding element to the exit of the at least one lateral side branch and delivering said subsequent covered stent through said catheter along the bendable guiding element for interconnection of covered stents and wherein the covered stents have a same dimension at the interconnection.

\* \* \* \* \*

UNITED STATES PATENT AND TRADEMARK OFFICE
CERTIFICATE OF CORRECTION

| | | |
|---|---|---|
| PATENT NO. | : 10,821,009 B2 | Page 1 of 1 |
| APPLICATION NO. | : 15/166141 | |
| DATED | : November 3, 2020 | |
| INVENTOR(S) | : Michael Szente Varga | |

It is certified that error appears in the above-identified patent and that said Letters Patent is hereby corrected as shown below:

On the Title Page

Item (12), delete "Varga" and insert --Szente Varga--.

Item (72), please amend the inventor's surname to read --Szente Varga--.

Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*